US008697356B2

(12) United States Patent (10) Patent No.: US 8,697,356 B2
Kim et al. (45) Date of Patent: Apr. 15, 2014

(54) SINGLE-MOLECULE-FORMAT PROBE AND UTILIZATION THEREOF

(75) Inventors: Sung-Bae Kim, Ibaraki (JP); Hiroaki Tao, Ibaraki (JP); Moritoshi Sato, Tokyo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 254 days.

(21) Appl. No.: 12/429,378

(22) Filed: Apr. 24, 2009

(65) Prior Publication Data

US 2009/0269781 A1 Oct. 29, 2009

(30) Foreign Application Priority Data

Apr. 25, 2008 (JP) ................. 2008-116098

(51) Int. Cl.
| | |
|---|---|
| C12Q 1/68 | (2006.01) |
| C12Q 1/66 | (2006.01) |
| G01N 33/53 | (2006.01) |
| G01N 33/566 | (2006.01) |
| C12N 5/02 | (2006.01) |
| C12N 9/02 | (2006.01) |
| C12N 15/00 | (2006.01) |
| C12N 9/96 | (2006.01) |
| C07H 21/04 | (2006.01) |

(52) U.S. Cl.
USPC ............... 435/6.1; 435/7.1; 435/7.2; 435/8; 435/188; 435/189; 435/325; 435/320.1; 435/455; 536/23.2; 536/24.3; 436/501

(58) Field of Classification Search
None
See application file for complete search history.

(56) References Cited

U.S. PATENT DOCUMENTS

2009/0113563 A1* 4/2009 Umezawa et al. ............. 800/14

FOREIGN PATENT DOCUMENTS

| CA | 2601952 | * | 8/2005 |
| WO | 2007-120522 A2 | | 10/2007 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Promega Technical Manual, Dual Luciferase, 2006.*

Awais et al., "A Fluorescent Indicator to Visualize Activities of the Androgen Receptor Ligands in Single Living Cells", Angew. Chem. Int. Ed., 2006, vol. 45, pp. 2707-2712.
Baird et al., "Circular Permutation and Receptor Insertion within Green Fluorescent Proteins", Proc. Natl. Acad. Sci. U.S.A., 1999, vol. 96, pp. 11241-11246.
Conti et al., "Crystal Structure of Firefly Luciferase Throws Light on a Superfamily of Adenylate-Forming Enzymes", Structure, 1996, vol. 4, No. 3, pp. 287-298.
Hodges et al., "Estrogen Receptors {alpha} and ss: Prevalence of Estrogen Receptor ss mRNA in Human Vascular Smooth Muscle and Transcriptional Effects", Circulation, 2000, vol. 101, pp. 1792-1798.
Kaihara et al., "Locating a Protein-Protein Interactions in Living Cells via Split Renilla Luciferase Complementation", Analytical Chemistry, 2003, vol. 75, pp. 4176-4181.
Kawai et al., "Single Color Fluorescent Indicators of Protein Phosphorylation for Multicolor Imaging of Intracellular Signal Flow Dynamics", Analytical Chemistry, 2004, vol. 76, pp. 6144-6149.
Kim et al., "Nongenomic Activity of Ligands in the Association of Androgen Receptor with Src", ACS Chemistry Biology, 2007, vol. 2, No. 7, pp. 484-492.
Kim et al., "High-throughput Sensing and Noninvasive Imaging of Protein Nuclear Transport by Using Reconstitution of Split Renilla Luciferase", PNAS 2004, vol. 101, No. 32, pp. 11542-11547.
Kim et al., "Integrated Molecule-Format Bioluminescent Probe for Visualizing Androgenicity of Ligands Based on the Intramolecular Association of Androgen Receptor with Its Recognition Peptide", Analytical Chemistry, 2007, vol. 79, No. 5, pp. 1874-1880.
Kim et al., "Bioluminescent Indicator for Determining Protein-Protein Interactions Using Intramolecular Complementation of Split Click Beetle Luciferase", Analytical Chemistry, 2007, vol. 79, No. 13, pp. 4820-4826.
Kotlikoff, Michael I., "Genetically Encoded Ca2+ Indicators: Using Genetics and Molecular Design to Understand Complex Physiology", J. Physiol. 2007, vol. 578, No. 1, pp. 55-67.
Maruvada et al, "Dynamics Shuttling and Intranuclear Mobility of Nuclear Hormone Receptors", The Journal of Biological Chemistry, 2003, vol. 278, No. 14, pp. 12425-12432.
Miyawaki et al., "Fluorescent Indicators for Ca2+ Based on Green Fluorescent Proteins and Calmodulin", Nature, 1997, vol. 388, pp. 882-887.
Paulmurugan et al., "Firefly Luciferase Enzyme Fragment Complementation for Imaging in Cells and Living Animals", Analytical Chemistry, 2005, vol. 77, pp. 1295-1302.
Paulmurugan et al., "An Intramolecular Folding Sensor for Imaging Estrogen Receptor-Ligand Interactions", PNAS, 2006, vol. 103, No. 43, pp. 15883-15888.

(Continued)

*Primary Examiner* — Iqbal H Chowdhury
(74) *Attorney, Agent, or Firm* — Edwards Wildman Palmer LLP

(57) ABSTRACT

A single-chain probe of the present invention for detecting a ligand, comprises: a ligand binding protein for binding the ligand; a recognition protein for recognizing that the ligand is bound by the ligand binding protein; and C- and N-terminal fragments, generated by dissecting an enzyme, between the ligand binding protein and the recognition protein, wherein a carboxy terminal end of the C-terminal fragment is located upstream of an amino terminal end of the N-terminal fragment, and the C- and N-terminal fragments vary the enzyme activity via complementation in case where the recognition protein recognizes that the ligand is bound by the ligand binding protein. This makes it possible to achieve detection of a target protein-specific ligand using the single chain with a high efficiency.

7 Claims, 22 Drawing Sheets

(56) References Cited

OTHER PUBLICATIONS

Remy et al., "A Highly Sensitive Protein-Protein Interaction Assay Based on *Gaussia* Luciferase", Nature Methods, 2006, vol. 3, No. 12, pp. 977-979.

Rich et al., "Kinetic Analysis of Estrogen Receptor/Ligand Interactions", PNAS, 2002, vol. 99, No. 13, pp. 8562-8567.

Souslova et al., "Genetically Encoded Intracellular Sensors Based on Fluorescent Proteins", Biochemistry (Moscow), 2007 vol. 72, No. 7, pp. 683-697.

Truong et al., "FRET-Based in vivo Ca2+ Imaging by A NEW Calmodulin-GFP fusion molecule", Nature Structural Biology, 2001, vol. 8, No. 12, pp. 1069-1073.

Tyagi et al., "Dynamics of Intracellular Movement and Nucleocytoplasmic Recycling of the Ligand-Activated Androgen Receptor in Living Cells", Molecular Endocrinology, 2000, Vo. 14, No. 8, pp. 1162-1174.

Varricchio et al., "Inhibition of Estradiol Receptor/Src Association and Cell Growth by an Estradiol Receptor a Tyrosine-Phosphorylated Peptide", Mol. Cancer Res., 2007, vol. 5, No. 11, pp. 1213-1221.

Vivian et al., "The Influence of Ala243 (Gty247), Arg215 and Thr226(Asn230) on the Bioluminescence Spectra and pH-Sensitivity of Railroad Worm, Click Beetle and Firefly Luciferases", Photochemistry and Photobiology, 2002, vol. 76, No. 5, pp. 538-544.

Weissleder et al., "Shedding Ligiat onto Live Molecular Targets", Nature Medicine, 2003, vol. 9, No. 1, pp. 123-128.

Zhong et al., "Mutations of Tyrosine 537 in the Human Estrogen Receptor-a Selectivity Alter the Receptor's Affinity for Estradiol and the Kinetics of the Interaction", Biochemistry, 2002, vol. 41, pp. 4209-4217.

Kim, Sung Bae, et al. "Development of Molecular Imaging Probes Based on Bioluminescence and Fluorescence", *Bunseki Kagaku*, vol. 58, No. 6, 2009, pp. 435-446.

Kim, Sung Bae, et al. "Circularly Permutated Bioluminescent Probes for Illuminating Ligand-Activated Protein Dynamics" *Bioconjugate Chemistry*, vol. 19, Dec. 2008, pp. 2480-2486.

Japanese Office Action mailed on Apr. 9, 2013, in corresponding Japanese Patent Application No. 2008-116098.

\* cited by examiner

SEQUENCE LISTING

```
<160> NUMBER OF SEQ ID NOS: 6

<210> SEQ ID NO 1
<211> LENGTH: 916
<212> TYPE: PRT
<213> ORGANISM: Artificial Sequence
<220> FEATURE:
<223> OTHER INFORMATION: Description of Artificial Sequence:Synthetic
      oligopeptide

<400> SEQUENCE: 1

Met Ser Leu Ala Leu Ser Leu Thr Ala Asp Gln Met Val Ser Ala Leu
  1               5                  10                  15

Leu Asp Ala Glu Pro Pro Ile Leu Tyr Ser Glu Tyr Asp Pro Thr Arg
                 20                  25                  30

Pro Phe Ser Glu Ala Ser Met Met Gly Leu Leu Thr Asn Leu Ala Asp
             35                  40                  45

Arg Glu Leu Val His Met Ile Asn Trp Ala Lys Arg Val Pro Gly Phe
         50                  55                  60

Val Asp Leu Thr Leu His Asp Gln Val His Leu Leu Glu Cys Ala Trp
     65                  70                  75                  80

Leu Glu Ile Leu Met Ile Gly Leu Val Trp Arg Ser Met Glu His Pro
                 85                  90                  95

Gly Lys Leu Leu Phe Ala Pro Asn Leu Leu Leu Asp Arg Asn Gln Gly
```

```
                        100                 105                 110
Lys Cys Val Glu Gly Met Val Glu Ile Phe Asp Met Leu Leu Ala Thr
            115                 120                 125

Ser Ser Arg Phe Arg Met Met Asn Leu Gln Gly Glu Phe Val Cys
    130                 135                 140

Leu Lys Ser Ile Ile Leu Leu Asn Ser Gly Val Tyr Thr Phe Leu Ser
145                 150                 155                 160

Ser Thr Leu Lys Ser Leu Glu Glu Lys Asp His Ile His Arg Val Leu
                165                 170                 175

Asp Lys Ile Thr Asp Thr Leu Ile His Leu Met Ala Lys Ala Gly Leu
            180                 185                 190

Thr Leu Gln Gln Gln His Gln Arg Leu Ala Gln Leu Leu Ile Leu
        195                 200                 205

Ser His Ile Arg His Met Ser Asn Lys Gly Met Glu His Leu Tyr Ser
    210                 215                 220

Met Lys Cys Lys Asn Val Val Pro Leu Tyr Asp Leu Leu Leu Glu Met
225                 230                 235                 240

Leu Asp Ala His Arg Leu His Gly Ser Gly Gly Lys Tyr Lys Gly
                245                 250                 255

Ser Gln Val Ala Pro Ala Glu Leu Glu Ile Leu Leu Lys Asn Pro
            260                 265                 270

Cys Ile Arg Asp Val Ala Val Gly Ile Pro Asp Leu Glu Ala Gly
            275                 280                 285

Glu Leu Pro Ser Ala Phe Val Val Lys Gln Pro Gly Thr Glu Ile Thr
    290                 295                 300

Ala Lys Glu Val Tyr Asp Tyr Leu Ala Glu Arg Val Ser His Thr Lys
305                 310                 315                 320

Tyr Leu Arg Gly Gly Val Arg Phe Val Asp Ser Ile Pro Arg Asn Val
                325                 330                 335

Thr Gly Lys Ile Thr Arg Lys Glu Leu Leu Lys Gln Leu Leu Val Lys
            340                 345                 350

Ala Gly Gly Gly Gly Gly Ser Gly Arg Gly Gly Gly Ser Met
        355                 360                 365

Val Lys Arg Glu Lys Asn Val Ile Tyr Gly Pro Glu Pro Leu His Pro
    370                 375                 380

Leu Glu Asp Leu Thr Ala Gly Glu Met Leu Phe Arg Ala Leu Arg Lys
385                 390                 395                 400

His Ser His Leu Pro Gln Ala Leu Val Asp Val Val Gly Asp Glu Ser
                405                 410                 415

Leu Ser Tyr Lys Glu Phe Phe Glu Ala Thr Val Leu Leu Ala Gln Ser
            420                 425                 430

Leu His Asn Cys Gly Tyr Lys Met Asn Asp Val Val Ser Ile Cys Ala
        435                 440                 445

Glu Asn Asn Thr Arg Phe Phe Ile Pro Val Ile Ala Ala Trp Tyr Ile
    450                 455                 460

Gly Met Ile Val Ala Pro Val Asn Glu Ser Tyr Ile Pro Asp Glu Leu
465                 470                 475                 480

Cys Lys Val Met Gly Ile Ser Lys Pro Gln Ile Val Phe Thr Thr Lys
                485                 490                 495

Asn Ile Leu Asn Lys Val Leu Glu Val Gln Ser Arg Thr Asn Phe Ile
            500                 505                 510

Lys Arg Ile Ile Ile Leu Asp Thr Val Glu Asn Ile His Gly Cys Glu
        515                 520                 525
```

```
Ser Leu Pro Asn Phe Ile Ser Arg Tyr Ser Asp Gly Asn Ile Ala Asn
            530                 535                 540

Phe Lys Pro Leu His Phe Asp Pro Val Glu Gln Val Ala Ala Ile Leu
545                 550                 555                 560

Cys Ser Ser Gly Thr Thr Gly Leu Pro Lys Gly Val Met Gln Thr His
                565                 570                 575

Gln Asn Ile Cys Val Arg Leu Ile His Ala Leu Asp Pro Arg Tyr Gly
            580                 585                 590

Thr Gln Leu Ile Pro Gly Val Thr Leu Val Tyr Leu Pro Phe Phe
            595                 600                 605

His Ala Phe Gly Phe His Ile Thr Leu Gly Tyr Phe Met Val Gly Leu
            610                 615                 620

Arg Val Ile Met Phe Arg Arg Phe Asp Gln Glu Ala Phe Leu Lys Ala
625                 630                 635                 640

Ile Gln Asp Tyr Glu Val Arg Ser Val Ile Asn Val Pro Ser Val Ile
                645                 650                 655

Leu Phe Leu Ser Lys Ser Pro Leu Val Asp Lys Tyr Asp Leu Ser Ser
                660                 665                 670

Leu Arg Glu Leu Cys Cys Gly Ala Ala Pro Leu Ala Lys Glu Val Ala
            675                 680                 685

Glu Val Ala Ala Lys Arg Leu Asn Leu Pro Gly Ile Arg Cys Gly Phe
690                 695                 700

Gly Leu Thr Glu Ser Thr Ser Ala Ile Ile Gln Thr Leu Gly Asp Glu
705                 710                 715                 720

Phe Lys Ser Gly Ser Leu Gly Arg Val Thr Pro Leu Met Ala Ala Lys
                725                 730                 735

Ile Ala Asp Arg Glu Thr Gly Lys Ala Leu Gly Pro Asn Gln Val Gly
            740                 745                 750

Glu Leu Cys Ile Lys Gly Pro Met Val Ser Lys Gly Tyr Val Asn Asn
            755                 760                 765

Val Glu Ala Thr Lys Glu Ala Ile Asp Asp Gly Trp Leu His Ser
770                 775                 780

Gly Asp Phe Gly Tyr Tyr Asp Glu Asp Glu His Phe Tyr Val Val Asp
785                 790                 795                 800

Arg Tyr Lys Glu Leu Ile Gly Gly Gly Thr Val Ala Pro Ser Asp
                805                 810                 815

Ser Ile Gln Ala Glu Glu Trp Tyr Phe Gly Lys Ile Thr Arg Arg Glu
            820                 825                 830

Ser Glu Arg Leu Leu Leu Asn Ala Glu Asn Pro Arg Gly Thr Phe Leu
            835                 840                 845

Val Arg Glu Ser Glu Thr Thr Lys Gly Ala Tyr Cys Leu Ser Val Ser
850                 855                 860

Asp Phe Asp Asn Ala Lys Gly Leu Asn Val Lys His Tyr Lys Ile Arg
865                 870                 875                 880

Lys Leu Asp Ser Gly Gly Phe Tyr Ile Thr Ser Arg Thr Gln Phe Asn
                885                 890                 895

Ser Leu Gln Gln Leu Val Ala Tyr Tyr Ser Lys His Ala Asp Gly Leu
            900                 905                 910

Cys His Arg Leu
        915

<210> SEQ ID NO 2
<211> LENGTH: 830
<212> TYPE: PRT
<213> ORGANISM: Artificial Sequence
```

<220> FEATURE:
<223> OTHER INFORMATION: Description of Artificial Sequence:Synthetic oligopeptide

<400> SEQUENCE: 2

```
Met Arg Gly Ala Phe Gln Asn Leu Phe Gln Ser Val Gly Ser Gly Gly
  1               5                  10                  15

Gly Gly Trp Leu His Ser Gly Asp Ile Ala Tyr Trp Asp Glu Asp Glu
             20                  25                  30

His Phe Phe Ile Val Asp Arg Leu Lys Ser Leu Ile Lys Tyr Lys Gly
         35                  40                  45

Tyr Gln Val Ala Pro Ala Glu Leu Glu Ser Ile Leu Leu Gln His Pro
     50                  55                  60

Asn Ile Phe Asp Ala Gly Val Ala Gly Leu Pro Asp Asp Asp Ala Gly
 65                  70                  75                  80

Glu Leu Pro Ala Ala Val Val Leu Glu His Gly Lys Thr Met Thr
                 85                  90                  95

Glu Lys Glu Ile Val Asp Tyr Val Ala Ser Gln Val Thr Thr Ala Lys
                100                 105                 110

Lys Leu Arg Gly Gly Val Val Phe Val Asp Glu Val Pro Lys Gly Leu
            115                 120                 125

Thr Gly Lys Leu Asp Ala Arg Lys Ile Arg Glu Ile Leu Ile Lys Ala
        130                 135                 140

Lys Lys Gly Gly Lys Ile Ala Val Gly Gly Gly Ser Gly Arg Gly
145                 150                 155                 160

Gly Gly Gly Ser Met Glu Asp Ala Lys Asn Ile Lys Lys Gly Pro Ala
                165                 170                 175

Pro Phe Tyr Pro Leu Glu Asp Gly Thr Ala Gly Glu Gln Leu His Lys
            180                 185                 190

Ala Met Lys Arg Tyr Ala Leu Val Pro Gly Thr Ile Ala Phe Thr Asp
        195                 200                 205

Ala His Ile Glu Val Asp Ile Thr Tyr Ala Glu Tyr Phe Glu Met Ser
    210                 215                 220

Val Arg Leu Ala Glu Ala Met Lys Arg Tyr Gly Leu Asn Thr Asn His
225                 230                 235                 240

Arg Ile Val Val Cys Ser Glu Asn Ser Leu Gln Phe Phe Met Pro Val
                245                 250                 255

Leu Gly Ala Leu Phe Ile Gly Val Ala Val Ala Pro Ala Asn Asp Ile
            260                 265                 270

Tyr Asn Glu Arg Glu Leu Leu Asn Ser Met Gly Ile Ser Gln Pro Thr
        275                 280                 285

Val Val Phe Val Ser Lys Lys Gly Leu Gln Lys Ile Leu Asn Val Gln
    290                 295                 300

Lys Lys Leu Pro Ile Ile Gln Lys Ile Ile Met Asp Ser Lys Thr
305                 310                 315                 320

Asp Tyr Gln Gly Phe Gln Ser Met Tyr Thr Phe Val Thr Ser His Leu
                325                 330                 335

Pro Pro Gly Phe Asn Glu Tyr Asp Phe Val Pro Glu Ser Phe Asp Arg
            340                 345                 350

Asp Lys Thr Ile Ala Leu Ile Met Asn Ser Ser Gly Ser Thr Gly Leu
        355                 360                 365

Pro Lys Gly Val Ala Leu Pro His Arg Thr Ala Cys Val Arg Phe Ser
    370                 375                 380

His Ala Arg Asp Pro Ile Phe Gly Asn Gln Ile Ile Pro Asp Thr Ala
385                 390                 395                 400
```

-continued

```
Ile Leu Ser Val Val Pro Phe His His Gly Phe Gly Met Phe Thr Thr
                405                 410                 415
Leu Gly Tyr Leu Ile Cys Gly Phe Arg Val Val Leu Met Tyr Arg Phe
            420                 425                 430
Glu Glu Glu Leu Phe Leu Arg Ser Leu Gln Asp Tyr Lys Ile Gln Ser
        435                 440                 445
Ala Leu Leu Val Pro Thr Leu Phe Ser Phe Ala Lys Ser Thr Leu
    450                 455                 460
Ile Asp Lys Tyr Asp Leu Ser Asn Leu His Glu Ile Ala Ser Gly Gly
465                 470                 475                 480
Ala Pro Leu Ser Lys Glu Val Gly Glu Ala Val Ala Lys Arg Phe His
                485                 490                 495
Leu Pro Gly Ile Arg Gln Gly Tyr Gly Leu Thr Glu Thr Thr Ser Ala
                500                 505                 510
Ile Leu Ile Thr Pro Glu Gly Asp Asp Lys Pro Gly Ala Val Gly Lys
                515                 520                 525
Val Val Pro Phe Phe Glu Ala Lys Val Val Asp Leu Asp Thr Gly Lys
    530                 535                 540
Thr Leu Gly Val Asn Gln Arg Gly Glu Leu Cys Val Arg Gly Pro Met
545                 550                 555                 560
Ile Met Ser Gly Tyr Val Asn Asn Pro Glu Ala Thr Asn Ala Leu Ile
                565                 570                 575
Asp Lys Asp Gly Gly Gly Gly Thr Ile Phe Leu Asn Val Leu Glu Ala
                580                 585                 590
Ile Glu Pro Gly Val Val Cys Ala Gly His Asp Asn Asn Gln Pro Asp
                595                 600                 605
Ser Phe Ala Ala Leu Leu Ser Ser Leu Asn Glu Leu Gly Glu Arg Gln
                610                 615                 620
Leu Val His Val Val Lys Trp Ala Lys Ala Leu Pro Gly Phe Arg Asn
625                 630                 635                 640
Leu His Val Asp Asp Gln Met Ala Val Ile Gln Tyr Ser Trp Met Gly
                645                 650                 655
Leu Met Val Phe Ala Met Gly Trp Arg Ser Phe Thr Asn Val Asn Ser
                660                 665                 670
Arg Met Leu Tyr Phe Ala Pro Asp Leu Val Phe Asn Glu Tyr Arg Met
                675                 680                 685
His Lys Ser Arg Met Tyr Ser Gln Cys Val Arg Met Arg His Leu Ser
                690                 695                 700
Gln Glu Phe Gly Trp Leu Gln Ile Thr Pro Gln Glu Phe Leu Cys Met
705                 710                 715                 720
Lys Ala Leu Leu Leu Phe Ser Ile Ile Pro Val Asp Gly Leu Lys Asn
                725                 730                 735
Gln Lys Phe Phe Asp Glu Leu Arg Met Asn Tyr Ile Lys Glu Leu Asp
            740                 745                 750
Arg Ile Ile Ala Cys Lys Arg Lys Asn Pro Thr Ser Cys Ser Arg Arg
            755                 760                 765
Phe Tyr Gln Leu Thr Lys Leu Leu Asp Ser Val Gln Pro Ile Ala Arg
            770                 775                 780
Glu Leu His Gln Phe Thr Phe Asp Leu Leu Ile Lys Ser His Met Val
785                 790                 795                 800
Ser Val Asp Phe Pro Glu Met Met Ala Glu Ile Ile Ser Val Gln Val
                805                 810                 815
Pro Lys Ile Leu Ser Gly Lys Val Lys Pro Ile Tyr Phe His
```

<210> SEQ ID NO 3
<211> LENGTH: 362
<212> TYPE: PRT
<213> ORGANISM: Artificial Sequence
<220> FEATURE:
<223> OTHER INFORMATION: Description of Artificial Sequence:Synthetic oligopeptide

<400> SEQUENCE: 3

Met Lys Arg Arg Trp Lys Lys Asn Phe Ile Ala Val Ser Ala Ala Asn
1               5                   10                  15

Arg Phe Lys Lys Ile Ser Ser Gly Ala Leu Gly Ser Gly Gly Gly
            20                  25                  30

Gly Ile Gly Glu Ala Ile Val Asp Ile Pro Glu Ile Pro Gly Phe Lys
        35                  40                  45

Asp Leu Glu Pro Met Glu Gln Phe Ile Ala Gln Val Asp Leu Cys Val
    50                  55                  60

Asp Cys Thr Thr Gly Cys Leu Lys Gly Leu Ala Asn Val Gln Cys Ser
65                  70                  75                  80

Asp Leu Leu Lys Lys Trp Leu Pro Gln Arg Cys Ala Thr Phe Ala Ser
                85                  90                  95

Lys Ile Gln Gly Gln Val Asp Lys Ile Lys Gly Ala Gly Gly Asp Lys
            100                 105                 110

Asp Glu Leu Gly Gly Arg Met Lys Pro Thr Glu Asn Asn Glu Asp Phe
        115                 120                 125

Asn Ile Val Ala Val Ala Ser Asn Phe Ala Thr Thr Asp Leu Asp Ala
    130                 135                 140

Asp Arg Gly Lys Leu Pro Gly Lys Lys Leu Pro Leu Glu Val Leu Lys
145                 150                 155                 160

Glu Met Glu Ala Asn Ala Arg Lys Ala Gly Cys Thr Arg Gly Cys Leu
                165                 170                 175

Ile Cys Leu Ser His Ile Lys Cys Thr Pro Lys Met Lys Lys Phe Ile
            180                 185                 190

Pro Gly Arg Cys His Thr Tyr Glu Gly Asp Lys Glu Ser Ala Gln Gly
        195                 200                 205

Gly Gly Gly Thr Met Ala Asp Gln Leu Thr Glu Glu Gln Ile Ala
    210                 215                 220

Glu Phe Lys Glu Ala Phe Ser Leu Phe Asp Lys Asp Gly Asp Gly Thr
225                 230                 235                 240

Ile Thr Thr Lys Glu Leu Gly Thr Val Met Arg Ser Leu Gly Gln Asn
                245                 250                 255

Pro Thr Glu Ala Glu Leu Gln Asp Met Ile Asn Glu Val Asp Ala Asp
            260                 265                 270

Gly Asn Gly Thr Ile Tyr Phe Pro Glu Phe Leu Thr Met Met Ala Arg
        275                 280                 285

Lys Met Lys Asp Thr Asp Ser Glu Glu Glu Ile Arg Glu Ala Phe Arg
    290                 295                 300

Val Phe Asp Lys Asp Gly Asn Gly Tyr Ile Ser Ala Ala Glu Leu Arg
305                 310                 315                 320

His Val Met Thr Asn Leu Gly Glu Lys Leu Thr Asp Glu Glu Val Asp
                325                 330                 335

Glu Met Ile Arg Glu Ala Asp Ile Asp Gly Asp Gly Gln Val Asn Tyr
            340                 345                 350

Glu Glu Phe Val Gln Met Met Thr Ala Lys

```
                355                 360

<210> SEQ ID NO 4
<211> LENGTH: 2757
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 4
atgagcctgg ccttgtccct gacggccgac cagatggtca gtgccttgtt ggatgctgag      60
ccccccatac tctattccga gtatgatcct accagaccct tcagtgaagc ttcgatgatg     120
ggcttactga ccaacctggc agacagggag ctggttcaca tgatcaactg ggcgaagagg     180
gtgccaggct ttgtggattt gaccctccat gatcaggtcc accttctaga atgtgcctgg     240
ctagagatcc tgatgattgg tctcgtctgg cgctccatgg agcacccagg gaagctactg     300
tttgctccta acttgctctt ggacaggaac cagggaaaat gtgtagaggg catggtggag     360
atcttcgaca tgctgctggc tacatcatct cggttccgca tgatgaatct gcagggagag     420
gagtttgtgt gcctcaaatc tattatttg cttaattctg gagtgtacac atttctgtcc     480 agcacccctga agtctctgga agagaaggac catatccacc gagtcctgga caagatcaca     540
gacactttga tccacctgat ggccaaggca ggcctgaccc tgcagcagca gcaccagcgg     600
ctggcccagc tcctcctcat cctctcccac atcaggcaca tgagtaacaa aggcatggag     660
catctgtaca gcatgaagtg caagaacgtg gtgcccctct atgacctgct gctggagatg     720
ctggacgccc accgcctaca tggatccgga ggcggcaaat acaagggtag ccaggttgct     780
ccagctgagt tggaggagat tctgttgaaa atccatgca ttcgcgatgt cgctgtggtc     840
ggcattcctg atctggaggc cggcgaactg ccttctgctt tcgttgtcaa gcagcctggt     900
acagaaatta ccgccaaaga gtgtatgat tacctggctg aacgtgtgag ccatactaag     960
tacttgcgtg gcggcgtgcg ttttgttgac tccatccctc gtaacgtaac aggcaaaatt    1020
acccgcaagg agctgttgaa acaattgttg gtgaaggccg gcgtggcgg cggtggcagc    1080 ggccgcggcg gaggtggcag catggtaaag cgtgagaaaa atgtcatcta tggccctgag    1140
cctctccatc ctttggagga tttgactgcc ggcgaaatgc tgtttcgtgc tctccgcaag    1200
cactctcatt tgcctcaagc cttggtcgat gtggtcggcg atgaatcttt gagctacaag    1260
gagttttttg aggcaaccgt cttgctggct cagtccctcc acaattgtgg ctacaagatg    1320
aacgacgtcg ttagtatctg tgctgaaaac aatacccgtt tcttcattcc agtcatcgcc    1380
gcatggtata tcggtatgat cgtggctcca gtcaacgaga gctacattcc cgacgaactg    1440
tgtaaagtca tgggtatctc taagccacag attgtcttca ccactaagaa tattctgaac    1500
aaagtcctgg aagtccaaag ccgcaccaac tttattaagc gtatcatcat cttggacact    1560
gtggagaata ttcacggttg cgaatctttg cctaatttca tctctcgcta ttcagacggc    1620
aacatcgcaa actttaaacc actccacttc gaccctgtgg aacaagttgc agccattctg    1680
tgtagcagcg gtactactgg actcccaaag ggagtcatgc agacccatca aaacatttgc    1740
gtgcgtctga tccatgctct cgatccacgc tacggcactc agctgattcc tggtgtcacc    1800
gtcttggtct acttgccttt cttccatgct ttcggctttc atattacttt gggttacttt    1860
atggtcggtc tccgcgtgat tatgttccgc cgttttgatc aggaggcttt cttgaaagcc    1920
atccaagatt atgaagtccg cagtgtcatc aacgtgccta gcgtgatcct gttttttgtct    1980 aagagcccac tcgtggacaa gtacgacttg tcttcactgc gtgaattgtg ttgcggtgcc    2040
```

```
gctccactgg ctaaggaggt cgctgaagtg gccgccaaac gcttgaatct tccagggatt    2100
cgttgtggct tcggcctcac cgaatctacc agtgcgatta tccagactct cggggatgag    2160
tttaagagcg gctctttggg ccgtgtcact ccactcatgg ctgctaagat cgctgatcgc    2220
gaaactggta aggctttggg cccgaaccaa gtgggcgagc tgtgtatcaa aggccctatg    2280
gtgagcaagg gttatgtcaa taacgttgaa gctaccaagg aggccatcga cgacgacggc    2340
tggttgcatt ctggtgattt tggatattac gacgaagatg agcattttta cgtcgtggat    2400
cgttacaagg agctgatcgg aggaggcggt accgtggcgc cctccgactc catccaggct    2460
gaggagtggt attttggcaa gatcaccaga cgggagtcag agcggttact gctcaatgca    2520
gagaacccga gagggacctt cctcgtgcga gaaagtgaga ccacgaaagg tgcctactgc    2580
ctctcagtgt ctgacttcga caacgccaag ggcctcaacg tgaagcacta caagatccgc    2640
aagctggaca cggcggcctt ctacatcacc tcccgcaccc agttcaacag cctgcagcag    2700
ctggtggcct actactccaa acacgccgat ggcctgtgcc accgcctctg actcgag       2757

<210> SEQ ID NO 5
<211> LENGTH: 2493
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 5
atgcgaggag cttttccagaa tctgttccag agcgtgggat ccggaggcgg cggatggcta     60
cattctggag acatagctta ctgggacgaa gacgaacact tcttcatcgt tgaccgcctg    120
aagtctctga ttaagtacaa aggctatcag gtggctcccg ctgaattgga atccatcttg    180
ctccaacacc ccaacatctt cgacgcaggt gtcgcaggtc ttcccgacga tgacgccggt    240
gaacttcccg ccgccgttgt tgtttttggag cacggaaaga cgatgacgga aaaagagatc    300
gtggattacg tcgccagtca agtaacaacc gcgaaaaagt tgcgcggagg agttgtgttt    360
gtggacgaag taccgaaagg tcttaccgga aaactcgacg caagaaaaat cagagagatc    420
ctcataaagg ccaagaaggg cggaaagatc gccgtgggcg gcggtggcag cggccgcggc    480
ggaggtggca gcatggaaga cgccaaaaac ataaagaaag gcccggcgcc attctatccg    540
ctggaagatg gaaccgctgg agagcaactg cataaggcta tgaagagata cgccctggtt    600
cctggaacaa ttgcttttac agatgcacat atcgaggtgg acatcactta cgctgagtac    660
ttcgaaatgt ccgttcggtt ggcagaagct atgaaacgat atgggctgaa tacaaatcac    720
agaatcgtcg tatgcagtga aaactctctt caattcttta tgccggtgtt gggcgcgtta    780
tttatcggag ttgcagttgc gcccgcgaac gacatttata tgaacgtga attgctcaac    840 agtatggca tttcgcagcc taccgtggtg ttcgtttcca aaaagggggtt gcaaaaaatt    900 ttgaacgtgc aaaaaaagct cccaatcatc caaaaaatta ttatcatgga ttctaaaacg    960
gattaccagg gatttcagtc gatgtacacg ttcgtcacat ctcatctacc tcccggtttt   1020
aatgaatacg attttgtgcc agagtccttc gatagggaca agacaattgc actgatcatg   1080
aactcctctg gatctactgg tctgcctaaa ggtgtcgctc tgcctcatag aactgcctgc   1140
gtgagattct cgcatgccag agatcctatt tttggcaatc aaatcattcc ggatactgcg   1200
attttaagtg ttgttccatt ccatcacggt tttggaatgt ttactacact cggatatttg   1260
atatgtggat ttcgagtcgt cttaatgtat agatttgaag aagagctgtt tctgaggagc   1320
```

| | |
|---|---|
| cttcaggatt acaagattca aagtgcgctg ctggtgccaa ccctattctc cttcttcgcc | 1380 |
| aaaagcactc tgattgacaa atacgattta tctaatttac acgaaattgc ttctggtggc | 1440 |
| gctcccctct ctaaggaagt cggggaagcg gttgccaaga ggttccatct gccaggtatc | 1500 |
| aggcaaggat atgggctcac tgagactaca tcagctattc tgattacacc cgaggggat | 1560 |
| gataaaccgg gcgcggtcgg taaagttgtt ccattttttg aagcgaaggt tgtggatctg | 1620 |
| gataccggga aaacgctggg cgttaatcaa agaggcgaac tgtgtgtgag aggtcctatg | 1680 |
| attatgtccg gttatgtaaa caatccggaa gcgaccaacg ccttgattga caaggatgga | 1740 |
| ggaggcggta ccatctttct gaatgtcctg gaagccattg agccaggtgt agtgtgtgct | 1800 |
| ggacacgaca acaaccagcc cgactccttt gcagccttgc tctctagcct caatgaactg | 1860 |
| ggagagagac agcttgtaca cgtggtcaag tgggccaagg ccttgcctgg cttccgcaac | 1920 |
| ttacacgtgg acgaccagat ggctgtcatt cagtactcct ggatggggct catggtgttt | 1980 |
| gccatgggct ggcgatcctt caccaatgtc aactccagga tgctctactt cgcccctgat | 2040 |
| ctggttttca atgagtaccg catgcacaag tcccggatgt acagccagtg tgtccgaatg | 2100 |
| aggcacctct ctcaagagtt tggatggctc caaatcaccc cccaggaatt cctgtgcatg | 2160 |
| aaagcactgc tactcttcag cattattcca gtggatgggc tgaaaaatca aaaattcttt | 2220 |
| gatgaacttc gaatgaacta catcaaggaa ctcgatcgta tcattgcatg caaaagaaaa | 2280 |
| aatcccacat cctgctcaag acgcttctac cagctcacca agctcctgga ctccgtgcag | 2340 |
| cctattgcga gagagctgca tcagttcact tttgacctgc taatcaagtc acacatggtg | 2400 |
| agcgtggact ttccggaaat gatggcagag atcatctctg tgcaagtgcc caagatcctt | 2460 |
| tctgggaaag tcaagcccat ctatttccac tga | 2493 |

```
<210> SEQ ID NO 6
<211> LENGTH: 1089
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 6
```

| | |
|---|---|
| atgaagaggc gctggaagaa aaacttcatt gccgtcagcg ctgccaaccg gttcaagaag | 60 |
| atctccagct ccggggcact gggatccgga ggcggcggca taggcgaggc gatcgtcgac | 120 |
| attcctgaga ttcctgggtt caaggacttg gagcccatgg agcagttcat cgcacaggtc | 180 |
| gatctgtgtg tggactgcac aactggctgc ctcaaagggc ttgccaacgt gcagtgttct | 240 |
| gacctgctca gaagtggct gccgcaacgc tgtgcgacct tgccagcaa gatccagggc | 300 |
| caggtggaca agatcaaggg ggccggtggt gacaaagacg aactgggcgg ccgcatgaag | 360 |
| cccaccgaga caacgaaga cttcaacatc gtggccgtgg ccagcaactt cgcgaccacg | 420 |
| gatctcgatg ctgaccgcgg gaagttgccc ggcaagaagc tgccgctgga ggtgctcaaa | 480 |
| gagatggaag ccaatgcccg gaaagctggc tgcaccaggg ctgtctgat ctgcctgtcc | 540 |
| cacatcaagt gcacgcccaa gatgaagaag ttcatcccag acgctgcca cacctacgaa | 600 |
| ggcgacaaag agtccgcaca gggcggagga ggcggtacca tggctgacca actgacagaa | 660 |
| gagcagattg cagagttcaa agaagccttc tcattattcg acaaggatgg ggacggcacc | 720 |
| atcaccacaa aggaacttgg caccgttatg aggtcgcttg gacaaaaccc aacggaagca | 780 |
| gaattgcagg atatgatcaa tgaagtcgat gctgatggca atggaacgat ttactttcct | 840 |
| gaatttctta ctatgatggc tagaaaaatg aaggacacag acagcgaaga ggaaatccga | 900 |

```
gaagcattcc gtgtttttga caaggatggc aacggctaca tcagcgctgc tgaattacgt      960
cacgtcatga caaacctcgg ggagaagtta acagatgaag aagttgatga aatgataagg     1020
gaagcagata tcgatggtga tggccaagta aactatgaag agtttgtaca aatgatgaca     1080
gcaaagtag                                                              1089
```

SINGLE-MOLECULE-FORMAT PROBE AND UTILIZATION THEREOF

This Nonprovisional application claims priority under 35 U.S.C. §119(a) on Patent Application No. 2008-116098 filed in Japan on Apr. 25, 2008, the entire contents of which are hereby incorporated by reference.

TECHNICAL FIELD

The present invention relates to a fusion protein for detecting a ligand in a subject sample and to utilization thereof. More specifically, the present invention relates to a fusion protein used as a single-molecule-format probe for detecting a target protein-specific ligand and to utilization thereof.

BACKGROUND ART

Revolutionary advances in molecular imaging technologies have allowed researchers to carry out quantitative examination of molecular dynamics and cell signaling in living cells (Non Patent Literature 1). As described in Non Patent literature 2, one of the imaging technologies with lighting protein is circular permutation (CP) of fluorescent proteins such as green fluorescent protein (GFP) for construction of probes. CP of GFP is a mutation in which the polypeptide of GFP is dissected and the N- and C-terminal fragments are inversely linked.

GFP has a conformation whose shape is a monolithic cylindrical symmetry wherein hydrophobic amino acids are serially arranged in a lattice manner. The principle of the circularly permutated probe with GFP is as follows. First, the fluorescence intensity from GFP is suppressed by water molecules accessing to the internal chromophore via a partially cleaved hole of GFP. The ligand recognition protein cofused to GFP closes the cleaved hole in response to a specific ligand. This causes the water molecule to be expelled from the chromophore, which results in enhancement of the fluorescence intensity. In this manner, the variation in the fluorescence intensities of GFP in the cells visualizes dynamics of molecular events in the cells.

The convention circular permutation of the fluorescent proteins was valid (i) only when the fluorescent proteins tolerates to insertion of a variety of proteins and (ii) only when the original N- and C-termini are spatially close enough to be linked (Non Patent Literature 13). The circular permutation of GFP required great skills because of their monolithic cylindrical symmetry and complexity of their protein strands. Thus, it was generally difficult to perform circular permutation.

Conventionally, the fluorescent proteins are suffered from an intrinsic problem that autofluorescence-caused elevation of background intensity. Further, fluorescent proteins requires an external light source and a relatively large instrumentation such as a fluorescence microscope for signalizing fluorescence. Autofluorescence inevitably causes an elevation of background intensity and poor signal-to-noise contrast in case of Yellow Camelleons (Non Patent Literatures 2 through 4) for example. In addition, the obtained results from fluorescent proteins are qualitative rather than quantitative because of the limited number of analyzable cell population at once (Non Patent Literature 5).

As a complement for the fluorescence proteins, bioluminescent proteins have been utilized in designing a new molecular probing system (Non Patent Literatures 5 through 9): e.g., providing a whole cell investigation; low background intensity; no external light sources.

Further, the present inventors demonstrated a single-molecule-format bioluminescent probe for imaging androgenic activities of ligands (Non Patent Literatures 10 and 11). The fundamental concept of single-molecule-format bioluminescent probe is to design a single-chain protein, in which all the components for signal recognition and light emission are integrated. In the single-molecule-format bioluminescent probe described in Non Patent Literatures 10 and 11, (i) a target ligand recognition protein and (ii) its interacting protein are sandwiched between the N- and C-terminal fragments of a dissected luciferase. The target ligand recognition protein activated by a ligand triggers an intramolecular complementation between the adjacent N- and C-terminal fragments in the bioluminescent probe. This complementation resulted in recovery or termination of the activities (exhibiting bioluminescence) of luciferase. The luminescence intensities were taken as a measure for visualizing molecular dynamics of ligand recognition proteins in cells.

CITATION LIST

Non Patent Literature 1

Weissleder, R.; Ntziachristos, V. Nat. Med. 2003, 9, 123-128.

Non Patent Literature 2

Souslova, E. A.; Chudakov, D. M. Biochemistry-Moscow 2007, 72, 683-697.

Non Patent Literature 3

Truong, K.; Sawano, A.; Mizuno, H.; Hama, H.; Tong, K. I.; Mal, T. K.; Miyawaki, A.; Ikura, M. Nat. Struc. Biol. 2001, 8, 1069-1073.

Non Patent Literature 4

Miyawaki, A.; Llopis, J.; Heim, R.; McCaffery, J. M.; Adams, J. A.; Ikura, M.; Tsien, R. Y. Nature 1997, 388, 882-887.

Non Patent Literature 5

Kim, S. B.; Ozawa, T.; Watanabe, S.; Umezawa, Y. Proc. Natl. Acad. Sci. U. S. A. 2004, 101, 11542-11547.

Non Patent Literature 6

Paulmurugan, R.; Gambhir, S. S. Anal. Chem. 2005, 77, 1295-1302.

Non Patent Literature 7

Paulmurugan, R.; Gambhir, S. S. Proc. Natl. Acad. Sci. U. S. A. 2006, 103, 15883-15888.

Non Patent Literature 8

Remy, I.; Michnick, S. W. Nat. Meth. 2006, 3, 977-979.

Non Patent literature 9

Kim, S. B.; Kanno, A.; Ozawa, T.; Tao, H.; Umezawa, Y. ACS Chem. Biol. 2007, 2, 484-492.

Non Patent literature 10

Kim, S. B.; Awais, M.; Sato, M.; Umezawa, Y.; Tao, H. Anal. Chem. 2007, 79, 1874-1880.

Non Patent literature 11

Kim, S. B.; Otani, Y.; Umezawa, Y.; Tao, H. Anal. Chem. 2007, 79, 4820-4826.

Non Patent Literature 12

Kotlikoff, M. I. J. Physiol. 2007, 578, 55-67.

Non Patent literature 13

Baird, G. S.; Zacharias, D. A.; Tsien, R. Y. Proc. Natl. Acad. Sci. U. S. A. 1999, 96, 11241-11246.

Non Patent literature 14

Conti, E.; Franks, N. P.; Brick, P. Structure 1996, 4, 287-298.

Non Patent Literature 15

Viviani, V. R.; Uchida, A.; Viviani, W.; Ohmiya, Y. Photochem. Photobiol. 2002, 76, 538-544.

Non Patent Literature 16

Kawai, Y.; Sato, M.; Umezawa, Y. Anal. Chem. 2004, 76, 6144-6149.

Non Patent Literature 17

Kaihara, A.; Kawai, Y.; Sato, M.; Ozawa, T.; Umezawa, Y. Anal. Chem. 2003, 75, 4176-4181.

Non Patent Literature 18

Varricchio, L.; Migliaccio, A.; Castoria, G.; Yamaguchi, H.; de Falco, A.; Di Domenico, M.; Giovannelli, P.; Farrar, W.; Appella, E.; Auricchio, F. Mol. Cancer Res. 2007, 5, 1213-1221.

Non Patent Literature 19

Rich, R. L.; Hoth, L. R.; Geoghegan, K. F.; Brown, T. A.; LeMotte, P. K.; Simons, S. P.; Hensley, P.; Myszka, D. G. Proc. Natl. Acad. Sci. U. S. A. 2002, 99, 8562-8567.

Non Patent Literature 20

Zhong, L.; Skafar, D. F. Biochemistry 2002, 41, 4209-4217.

Non Patent Literature 21

Tyagi, R. K.; Lavrovsky, Y.; Ahn, S. C.; Song, C. S.; Chatterjee, B.; Roy, A. K. Mol. Endocrinol. 2000, 14, 1162-1174.

Non Patent Literature 22

Maruvada, P.; Baumann, C. T.; Hager, G. L.; Yen, P. M. J. Biol. Chem. 2003, 278, 12425-12432.

Non Patent Literature 23

Awais, M.; Sato, M.; Lee, X. F.; Umezawa, Y. Angew. Chem. Int. Ed. 2006, 45, 2707-2712.

Non Patent Literature 24

Hodges, Y. K.; Tung, L.; Yan, X. D.; Graham, J. D.; Horwitz, K. B.; Horwitz, L. D. Circulation 2000, 101, 1792-1798.

However, the bioluminescent probe as an alternative of the fluorescent means also comprises limitations in the sensorial efficiency such as selectivities and detection limits upon ligand-sensing. Hence, development of a new probe has been highly required.

The present invention was made in view of the foregoing problems, and an object thereof is to provide a novel probe which can detect a ligand with high sensorial efficiency.

SUMMARY OF INVENTION

The present inventors intensively investigated the solution of the foregoing problems. Consequently, they invented a probe which can determine a ligand with high sensorial efficiency by dissecting an enzyme into two fragments and fabricating circular permutation. Particularly, they found that circular permutation of luciferase fragments inside a single-chain probe greatly suppresses the background enzyme activity.

The initial technical hurdle upon construction of the single-molecule-format (or simply single chain) probe was to find an appropriate dissection site of an enzyme that (i) temporally inactivates the enzyme by the suitable dissection of the enzyme into two fragments and warrants such convenient recovery of its activity only when a ligand is supplemented, (ii) allows the dissected enzyme to be stably expressed in mammalian cells after the permutation, without any decomposition or permanent inactivation, and (iii) allows the enzyme to tolerate to insertion of signal recognition proteins. The second hurdle was to determine an appropriate insertion protein that (i) does not destroy the total balance of the host probe, and (ii) is sensitive enough to ligands or is able to recruit other proteins upon ligand activation. The third hurdle was to optimize the size and position of each component protein in the probe for both (i) minimizing steric hindrance among the component proteins and (ii) maximizing signal-to-noise ratios.

Here, the feasibility of the bioluminescent probe carrying circularly permutated luciferases was explored with well-known luciferases derived from firefly (FLuc), Gaussia (GLuc), and click beetle (CBLuc).

The present inventors first constructed a bioluminescent probe carrying circularly permutated CBLuc. The original N- and C-termini of CBLuc were linked with a GS linker, and new N- and C-termini were created at between 1439 and K440 of CBLuc. The newly created termini of the circularly permutated CBLuc were linked with estrogen receptor ligand binding domain (ER LBD) and SH2 domain (Src SH2) of Src. The probe sensitively recognized 4-hydroxytamoxifen (OHT) known as an anticarcinogenic reagent for treating breast cancer and emitted specific bioluminescence.

The present inventors also identified an optimal fragmentation site of GLuc, the smallest bioluminescent protein, for CP. The original N- and C-termini were linked with a GS linker, while new N- and C-termini were created at between Gln105 and Gly106 of GLuc. The new N- and C-termini were respectively linked with a calmodulin-binding peptide (M13) of myosin light-chain kinase and calmodulin (CaM). This fusion protein was surprisingly stable and efficiently expressed in mammalian cells, and tolerated to insertion of M13 and CaM. CaM sensed endogenous calcium ion ($Ca^{2+}$) and recruited M13 located at the other end of the fusion protein. This binding exerted an approximation between the N- and C-terminal fragments of GLuc. This resulted in recovery of the enzyme activity.

Further, in order to determine the optimal fragmentation site of the luciferases, CBLuc and GLuc, the present inventors examined an optimal fragmentation site on the basis of a molecular structural information of Fluc belonging to the acyl-A-coenzyme family whose crystal structure had already been clarified. On the other hand, crystal structures of cBLuc and GLuc have not been reported yet. The molecular structure of FLuc is characterized in that: (i) FLuc consists of two dominant subdomains; and (ii) the putative active site exists in the vicinity of the linkage site between the domains (Non Patent Literatures 14 and 15). The two domains are linked with hydrophilic amino acids. According to two-dimensional hydrophobicity search on many luciferases, it is hypothesized that the optimal fragmentation site exists in the hydrophilic linkage site between the two subdomains. Based on such hypothesis, the present inventors finally found an optimal fragmentation site for CP.

Through the aforementioned studies performed by the present inventors, a bioluminescent probe including circularly permutated GLuc (cpGLuc) illuminated the real-time dynamics of $Ca^{2+}$ as a representative second messenger, and a bioluminescent probe including circularly permutated FLuc (cpFLuc) visualized specific interactions between proteins. A bioluminescent probe including circularly permutated CLuc (cpCLuc) imaged phosphorylation of an estrogen receptor (ER). Particularly, the background light by the bioluminescent probe comprising circularly permutated cpCBLuc decreased down to $1/1000$, while the background luminescence in the bioluminescent probe including circularly permutated cpGLuc decreased down to $1/100$. As a result, the present inventors found that the signal-to-noise ratios were extremely high under this condition. It should be noted that both $Ca^{2+}$ and estrogen are respectively a typical second messenger and a major steroid hormone. Hence, the upper examples using GLuc and CBLuc demonstrate general applicability of the present CP concept upon visualization of protein-protein interactions in living mammalian cells.

The mechanism of the presently invented bioluminescent probe based on the circularly permutated luciferase is conceptionally different from the conventional one using circularly permutated GFP (cpGFP): On/off system of fluorescent probes with cpGFP depends on the broken β sheet causing variation in the hydrophobicity of the fluorescent chromophore. On the other hand, the recovery of luminescence in the present bioluminescent probe is based on the physical approximation and dissociation between the completely separated luciferase fragments. Consequently, any example in which the luciferase is circularly permutated like the present invention has not been reported.

Because GFP and luciferase have completely different molecular structure and lighting chemistry, the bioluminescent probe constructed by the present inventors should be explained with a distinctive response mechanism to ligands and detection targets. Particularly, an insertion of peptides at the β sheet linkers temporarily disrupts fluorescence, owing to solvent penetration within the protein core, which interferes with the fluorophore-β sheet interactions (Non Patent Literature 12). The disrupting action is highly relieved through discharge of water molecule from the core caused by an interaction between the inserted proteins (Non Patent Literatures 13 and 16). However, this hydrophobicity explanation is not appropriate for the present probe carrying CP luciferase. It is because the enzyme active sites of luciferases consist of hydrophilic amino acids unlike the chromophore of GFP variants. This fundamental difference in the molecular mechanism for light emission makes it possible for the present bioluminescent probe to improve the ratio of the signal light to the background light (i.e., Signal-to-Noise (S/N) ratio).

As described above, in order to address to the foregoing problems, the present single-chain probe was invented for detecting a ligand, comprising: (i) a ligand binding protein for sensing the ligand; (ii) a recognition protein for identifying the ligand-activated ligand binding protein; and (iii) C- and N-terminal fragments of an enzyme, sandwiched between the ligand binding protein and the recognition protein, where an enzyme has been dissected into C- and N-terminal fragments, and a carboxy terminal of the C-terminal fragment is located upstream of an amino terminal of the N-terminal fragment. The C- and N-terminal fragments reconstitute the enzymatic activity via intramolecular complementation only when the recognition protein binds the ligand.

A polynucleotide according to the present invention encodes a fusion protein according to the present invention.

A polynucleotide according to the present invention is: the chimera DNA comprising a DNA sequence specified in any one of SEQ ID Nos: 4 through 6; a DNA sequence, in which nucleotides encoding one or several amino acids have been deleted, substituted, or added in the DNA sequence specified in any one of SEQ ID Nos: 4 through 6, said DNA sequence encoding a single-chain fusion protein in which two fragments of a dissected luciferase alter the luminescence intensity via intramolecular complementation in case where a recognition protein identifies the ligand-activated ligand binding protein; a DNA sequence which is hybridized with a polynucleotide, having a DNA sequence complementary with the DNA sequence specified in any one of SEQ ID Nos: 4 through 6, under a stringent condition, said DNA sequence encoding the fusion protein so that the two fragments of the luciferase having been dissected alter luminescence intensity of the luciferase via complementation in case where the recognition protein recognizes that the ligand is bound to the ligand binding protein; or a DNA sequence which is at least 66% identical to the base sequence specified in any one of SEQ ID Nos: 4 through 6, said DNA sequence encoding the fusion protein in which the two fragments of the luciferase having been dissected alter the luminescence intensity via complementation in case where the recognition protein recognizes that the ligand is bound to the ligand binding protein.

A vector according to the present invention comprises a polynucleotide according to the present invention. Further, a transformant according to the present invention comprises a polynucleotide according to the present invention. Also, a transformant according to the present invention comprises a vector according to the present invention.

A method according to the present invention is a method for detecting a ligand in a subject sample, and said method comprises the procedure of bringing the subject sample into contact with cell lines carrying a fusion protein probe according to the present invention.

A luminescent probe construction method according to the present invention comprises the procedure of transfecting a cell by using a polynucleotide according to the present invention. Further, a luminescent probe-contained detection kit according to the present invention comprises a polynucleotide according to the present invention.

A luminescent probe-based construction method according to the present invention comprises the step of transfecting a cell with a vector according to the present invention. A probe construction kit according to the present invention comprises a vector according to the present invention.

A luminescent probe-based method, according to the present invention, in which a fusion protein for detecting a ligand is constructed, and said method comprises the steps of: (i) dissecting a luciferase into C- and N-terminal fragments; and (ii) linking the C- and N-terminal fragments between a ligand binding protein for sensing the ligand and a recognition protein for recognizing that the ligand is bound to the ligand binding protein, wherein a carboxy terminal end of the C-terminal fragment is located at the upstream of the amino terminal end of the N-terminal fragment, and the correspondent carboxyl and amino terminal ends were linked with a GS linker.

For a fuller understanding of other objects, characteristics, and advantages of the invention, reference should be made to the ensuing detailed description taken in conjunction with the accompanying drawings.

DESCRIPTION OF EMBODIMENTS

[1. Fusion Protein and Polynucleotide]

Figure 1:
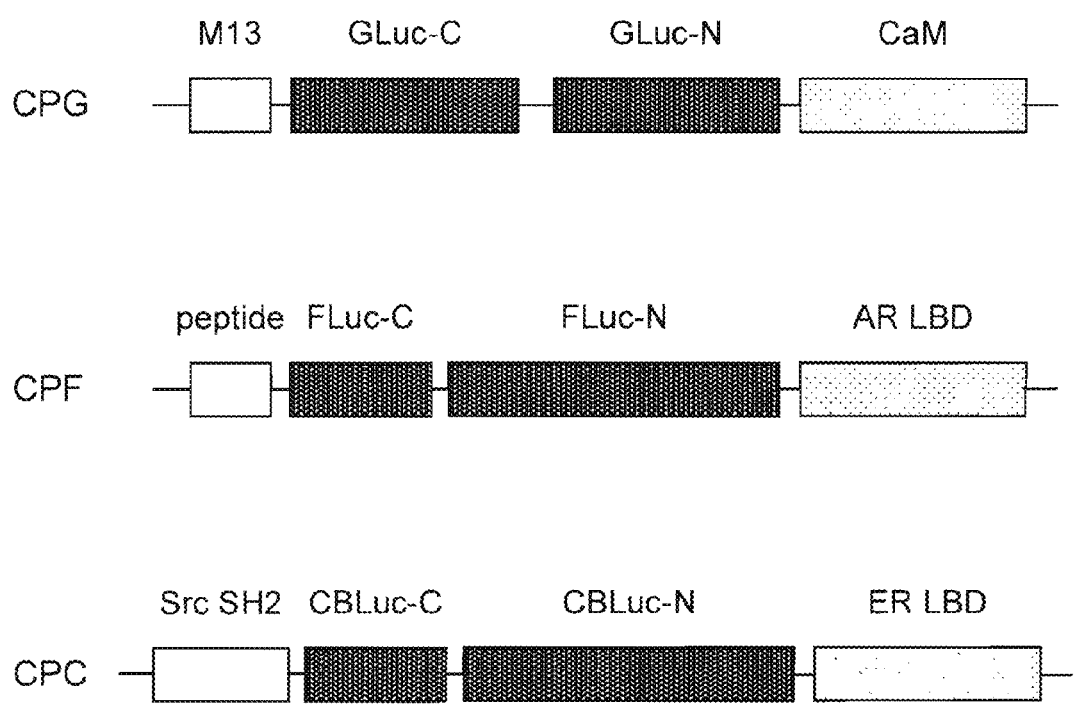
FIG. 1 is a conceptual diagram illustrating bioluminescent probes each containing circularly permutated luciferases according to the present invention.

A fusion protein according to the present invention is used in form of a single-molecule-format probe and detects a ligand, and comprises: a ligand binding protein for binding the ligand; a recognition protein for sensing that the ligand is bound to the ligand binding protein; and C- and N-terminal fragments, generated by dissecting an enzyme, sandwiched between the ligand binding protein and the recognition protein, wherein a carboxy terminal end of the C-terminal fragment is located upstream of an amino terminal end of the N-terminal fragment, and the C- and N-terminal fragments alter enzyme activity via an intramolecular complementation in case where the recognition protein recognizes that the ligand is bound to the ligand binding protein.

In the present specification, the "probe" may be a "bioluminescent probe" or a "luminescent probe" and is capable of visualizing various molecular phenomena, caused by a specific ligand, in living cells or living organisms. Further, the "single-molecule-format probe" is characterized by integrating all the components for ligand-sensing and light-emission in a single-molecular backbone. For example, the present single-molecule-format probe includes (i) the ligand binding protein, (ii) the recognition protein, (iii) the C-terminal fragment of the enzyme and (iv) the N-terminal fragment of the enzyme, as the basic components. Hereinafter, the fusion protein according to the present invention is sometimes referred to also as "probe" in view of its function.

Here, the "ligand binding protein" denotes a protein whose ligand binding site senses the ligand. The ligand binding protein, for example, is a protein which changes in its conformation upon ligand sensing and which can finally interact with the below described "recognition protein". Examples of the ligand binding protein include: a nuclear receptor (NR) sensing a hormone, a chemical compound, or a signaling protein as a ligand; a cytokine receptor; and various kinds of protein kinase. The ligand binding protein is suitably selected according to a target ligand. The ligand is not particularly limited as long as the ligand can be bound to the ligand binding protein. The ligand may be an exogenous ligand applied to the cell or may be an endogenous ligand newly generated in the cell in response to an outer stimulator. For example, the ligand can be an agonist or an antagonist for a receptor protein (e.g., a nuclear receptor, a G protein binding receptor, or the like). Further, examples of the ligand include: a signaling protein, specifically bound to a signal transduction protein in the cell, e.g., cytokine, chemokine, insulin, or the like; an intracellular second messenger; a lipid second messenger; a phosphorylated amino acid residue; a G-protein binding receptor ligand; and the like.

For example, in case of targeting an intracellular second messenger, a lipid second messenger, or the like as the ligand, a specific binding domain for each second messenger can be used as the ligand binding protein. The second messenger denotes an endogenous signal transmitter newly generated when an exogenous stimulator such as a neurotransmitter is bound to the specific receptor localized on a cell membrane. The second messenger includes cGMP, cAMP, PIP, $PIP_2$, $PIP_3$, inositol triphosphate ($IP_3$), $IP_4$, $Ca^{2+}$, diacylglycerol, arachidonic acid, and the like. For example, for $Ca^{2+}$ as a representative second messenger, calmodulin (CaM) serving as the ligand binding protein can be used.

Further, upon determination of a ligand stimulating a nuclear receptor for example, the known ligand binding domain (LBD) of the nuclear receptor can be adapted. Upon determination of a phosphorylated amino acid residue or a G protein binding receptor ligand, the phosphorylated amino acid binding domain or the G-protein binding receptor can be incorporated. As the nuclear receptor ligand binding domain (NR LBD), it is possible to favorably use (i) the ligand binding domain of an estrogen receptor (ER), (ii) the ligand binding domain of a glucocorticoid receptor (GR), (iii) the ligand binding domain of an androgen receptor (AR), or (iv) the ligand binding domain of a progesterone receptor (PR).

For example, in case of using estrogen receptor, the known LBD region (amino acid numbers 305 to 550) can be fused in the probe backbone using a genetic manipulation like a PCR synthesis on the basis of the sequence information (GenBank/P00372) on the full-length human estrogen receptor. In case of using the LBD of androgen receptor, the LBD region (amino acid numbers 672 to 910) can be used with a genetic manipulation like a PCR synthesis on the basis of the sequence information (GenBank/AF162704) of the full-length human androgen receptor. In case of using the LBD of glucocorticoid receptor, the ligand binding domain (amino acid numbers 527 to 777) can be added in the probe backbone using a genetic manipulation like a PCR synthesis on the basis of the sequence information (GenBank/1201277A) of the full-length human glucocorticoid receptor. In case of using the LBD of the progesterone receptor, the LBD region (amino acid numbers 677 to 933) can be genetically incorporated in the probe backbone through PCR synthesis on the basis of sequence information (GenBank/P06401) of the full-length human progesterone receptor.

In the present specification, the "recognition protein" denotes a protein which recognizes that the ligand is bound to the ligand binding protein. For example, the "recognition protein" indicates a protein recognizing the conformational change of ligand-stimulated LBD.

As a counterpart of calmodulin as the ligand binding protein, M13 peptide derived from myosin light chain kinase is recommended as the recognition protein. As a counterpart of calmodulin, CaM-dependent protein kinases such as adenyl cyclase, calmodulin kinase II, and the like can be adapt instead of M13. A truncated peptide of the proteins can be also used instead of the M13 protein.

As the counterpart of the nuclear receptors such as AR and ER, specific peptides like LXXLL, FQNLF, FXXLF motifs derived from a coactivator, can be used as the recognition protein (here, "X" means any amino acid). It is preferable to use LXXLL motif (ca. 15 amino acids) derived from coactivators such as Rip140 (GenBank/NP003480) or Src-la (steroid receptor coactivator 1 isoform 1; GenBank/NP003734).

Further, the SH2 domain of various kinases recognizing a phosphorylated amino acid residue may be used as the recognition protein. For example, it is possible to use: phosphorylation recognition domain (SH2 domain; amino acid numbers 150 to 248) of Src (proto-oncogene tyrosine-protein kinase Src; GenBank/NP938033) which is an anti-carcinogenic protein; SH2 domain of growth factor receptor-binding protein 2 (Grb2) associated with cell growth, carcinogenesis, and the like; and a similar domain. As the counterpart of the G protein binding receptor, a G protein or the like can be favorably used as the corresponding recognition protein.

In the present specification, the "enzyme" can be completely dissected into two fragments, i.e., N- and C-terminal fragments, and the two fragments of the dissected enzyme alter enzyme activity via complementation in case where the recognition protein recognizes that the ligand is bound to the ligand binding protein. A typical example of the enzyme is a lighting enzyme (LE). The N-terminal half of the dissected lighting enzyme is referred to also as "N-LE" and the C-terminal half of the dissected lighting enzyme is referred to also as "C-LE". The lighting enzymes consume firefly luciferin, *Renilla* luciferin, or lipid as its substrate the "enzyme" comprises firefly luciferase (FLuc), Gaussia luciferase (GLuc), click beetle luciferase (CBLuc), *Renilla* luciferase (RLuc), railroad worm luciferase, and the like.

An enzyme applicable to the circular permutation of the present invention includes oxidoreductase, transferase, hydrolase, lyase, isomerase, ligases, and the like. Specifically, the following applicability can be expected. glucose oxidase, i.e., the dimmer is circularly permutated to be temporarily inactivated. Thereafter, only in response to an external signal, the permutated fragments are reconstituted so that the oxidation activity to glucose is recovered. This oxidation activation is applicable to measurement of a blood glucose level. Further, the most important monomer of lactase is inactivated by circular permutation, and the hydrolyzed activity variance of lactose in response to outer stimulate can be measured. The assay system is applicable to various biological samples. An assay system using hydrolysis activity of esterase such as trypsin can be constructed. Further, an electrochemical sensor using enzyme activity of oxidoreductase such as NAD can be constructed.

As to these luciferases, the amino acid sequence and the genetic (DNA) base sequence are publicly known (e.g., GenBank/AB062786 and the like of FLuc, and GenBank/AY258592.1 and the like of CBLuc, GenBank/AY015993 and the like of GLuc). On the basis of the sequence information, it is possible to obtain the DNA sequences by a publicly known method.

The following exemplifies luciferases as an enzyme incorporated in the fusion protein according to the present invention, and the fusion protein according to the present invention is referred to also as a luminescent probe, but the present invention is not limited to this. Also other enzyme will be explained in the same manner.

Figure 3:
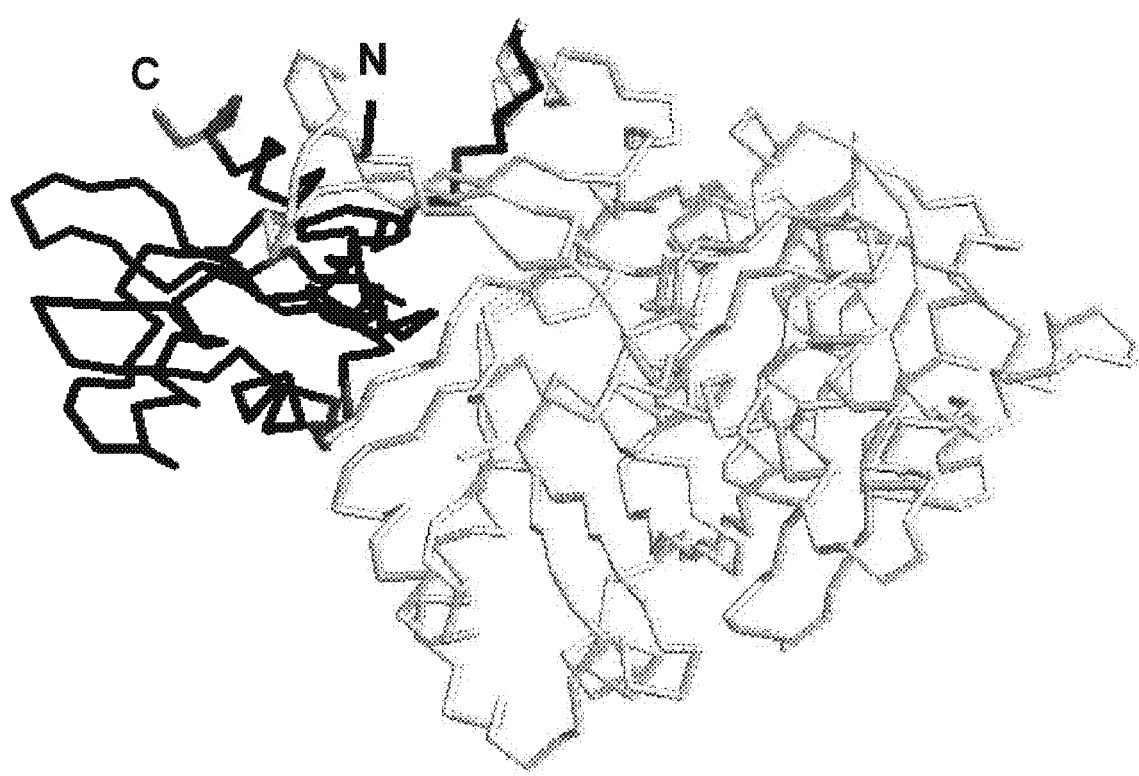
FIG. 3 is a crystal structure of firefly luciferase.

The present invention describes a polypeptide used as a single-molecule-format probe and is characterized in that a luciferase incorporated in the polypeptide is circularly permutated. The circular permutation means a genetic manipulation for enzymes in which original N- and C-termini of the enzyme are linked with an appropriate linker, and a specific dissection site in the sequence is made to create new N- and C-termini, wherein the fragments are replaced with each other so that the N-terminal amino acid sequence generated by luciferase dissection is located in the downstream of the C-terminal amino acid sequence. FIG. 3 illustrates a crystal structure of FLuc as an example of the conformation of the luciferase.

Here, the "luciferase dissected into two fragments" denotes a luciferase temporarily inactivated by dissecting a luciferase, i.e., a single protein, into two fragments. The luciferase is circularly permutated in the present invention. Thus, it is necessary to dissect the luciferase at a site which allows for such favorable reconstitution that the circularly permutated fragments of the dissected luciferase are physically approximated to each other and reconstitute the luminescent activity via complementation. Here, the "complementation" is the synonymous of self complementation of the fragments of the dissected luciferase.

The site at which the luciferase is dissected can be suitably set with reference to publicly known information. By dissecting the luciferase at an appropriate site and examining whether the luminescence intensity varies, person skilled in the art could easily determine an optimal dissection site. Further, the present inventors anticipated that a hydrophilic region exists between two subdomains constituting the luciferase. Thus, the dissection site may be estimated in accordance with information obtained by hydrophobicity search on the amino acid sequence of the luciferase.

As disclosed by Non Patent Literature 6, the luciferase may be dissected at between 437 and 438 of the amino acids sequence of FLuc for example. As described in the below Examples, FLuc may be dissected at between 415 and 416. Further, it is known that CBLuc can be dissected at between 412 and 413 or between 439 and 440 of CBLuc. Also in case of GLuc, GLuc may be dissected at a publicly known site, i.e., between 109 and 110. As described in the present Examples, the luciferase may be dissected at between 105 and 106. Further, the amino acid sequence of each fragment of the dissected luciferase may be partially duplicated or truncated.

In the present invention, the putative active site of the luciferase should be split in two portions and placed in the opposite side in the probe backbone, where each fragment of the split luciferase should comprise at least a minimal portion of the active site. In the luminescent probe according to the present invention, the binding of the probe to the ligand triggers the conformation change, so that, inside the probe, the ligand binding protein and the recognition protein are bound to each other, and the adjacent C-LE and N-LE are physically approximated. This reconstitutes the enzyme activity of the luciferase. Thus, in each of C-LE and N-LE, the active site of the luciferase is located at the end side of the probe (the side to which the ligand binding protein or the recognition protein is bound). This makes it possible to more surely recover the luminescent activity.

The respective components constituting the luminescent probe according to the present invention are tandemly linked without a linker or with an optimal linker peptide so as to be a single-chain fusion protein. In case of linking the components with a linker peptide, a distance between the respective components can be suitably adjusted by changing a kind and a length of the linker sequence. As a result, it is possible to optimize the spatial match of the fragments of the dissected luciferase.

The linker peptide is preferably such that the luminescent probe according to the present invention is expressed as a single-chain fusion protein. Further, it is preferable that the linkage is performed with a linker peptide which contains, as a main component, a highly flexible amino acid (glycine (G), alanine (A), or the like) for minimizing steric hindrance and a part of Serine (S) is added for further giving hydrophilicity so that self complementation does not occur before the two fragments of the dissected luciferase are physically approximated by a ligand. As such a linker peptide, it is preferable to use a GS linker, consisting of a glycine and serine repetitive sequence, whose length is substantially equal to 1 to 10 amino acid(s), and it is more preferable to use a GS linker, consisting of a glycine and serine repetitive sequence, whose length is substantially equal to 5 to 10 amino acids.

The components of the luminescent probe according to the present invention can be linked in any order as long as the circularly permutated luciferase is located between the ligand binding protein and the recognition protein, but it is preferable that the recognition protein, C-LE, N-LE, and the ligand binding protein are tandemly linked in this order. In other words, it is preferable that C-LE is located downstream of the recognition protein, and N-LE is located downstream of C-LE, and the ligand binding protein is located downstream of N-LE. FIG. 1 is a conceptual diagram illustrating an example of the luminescent probes according to the present invention.

As illustrated in FIG. 1, in case of using CaM as the ligand binding protein and using M13 as the recognition protein to detect $Ca^{2+}$, it is preferable that C-LE is linked to M13 and N-LE is linked to CaM. In this case, it is preferable that GLuc is circularly permutated as the luciferase, and C-LE (GLuc-C) of GLuc and N-LE (GLuc-N) of GLuc are arranged in this order. Specifically, M13, GLuc-C, GLuc-N, and CaM are tandemly linked in this order from the side of the N-terminal. The structural rearrangement of the components in the luminescent probe in this manner is reversible, so that association or dissociation of $Ca^{2+}$ to the probe can be imaged in real time. Further, the luminescent probe does not serve exogenous stimulator directly, but recognize the second messenger newly generated as an intercellular secondary phenomenon caused by the exogenous stimulator, so that the structure changes. Thus, the ligand does not have to be passed in to the plasma membrane of the cell. A natural signal amplification mechanism of a receptor on the cell membrane is used, so that the luminescent probe immediately recognizes the amplified signal.

In order to detect a ligand which phosphorylates LBD of the estrogen receptor, ER LBD is used as the ligand binding protein and a phosphorylated recognition domain (Src SH2) of Src is cofused as the recognition protein. It is preferable that C-LE is linked to SH2, while N-LE is linked to LBD. In this case, it is preferable that CBLuc is circularly permutated as the luciferase, and the corresponding C-LE (CBLuc-C) of CBLuc and N-LE (CBLuc-N) of CBLuc are placed in this order in the probe. Specifically, Src SH2, CBLuc-C, CBLuc-N, and ER LBD are tandemly linked in this order from the side of the N terminal.

Figure 2:
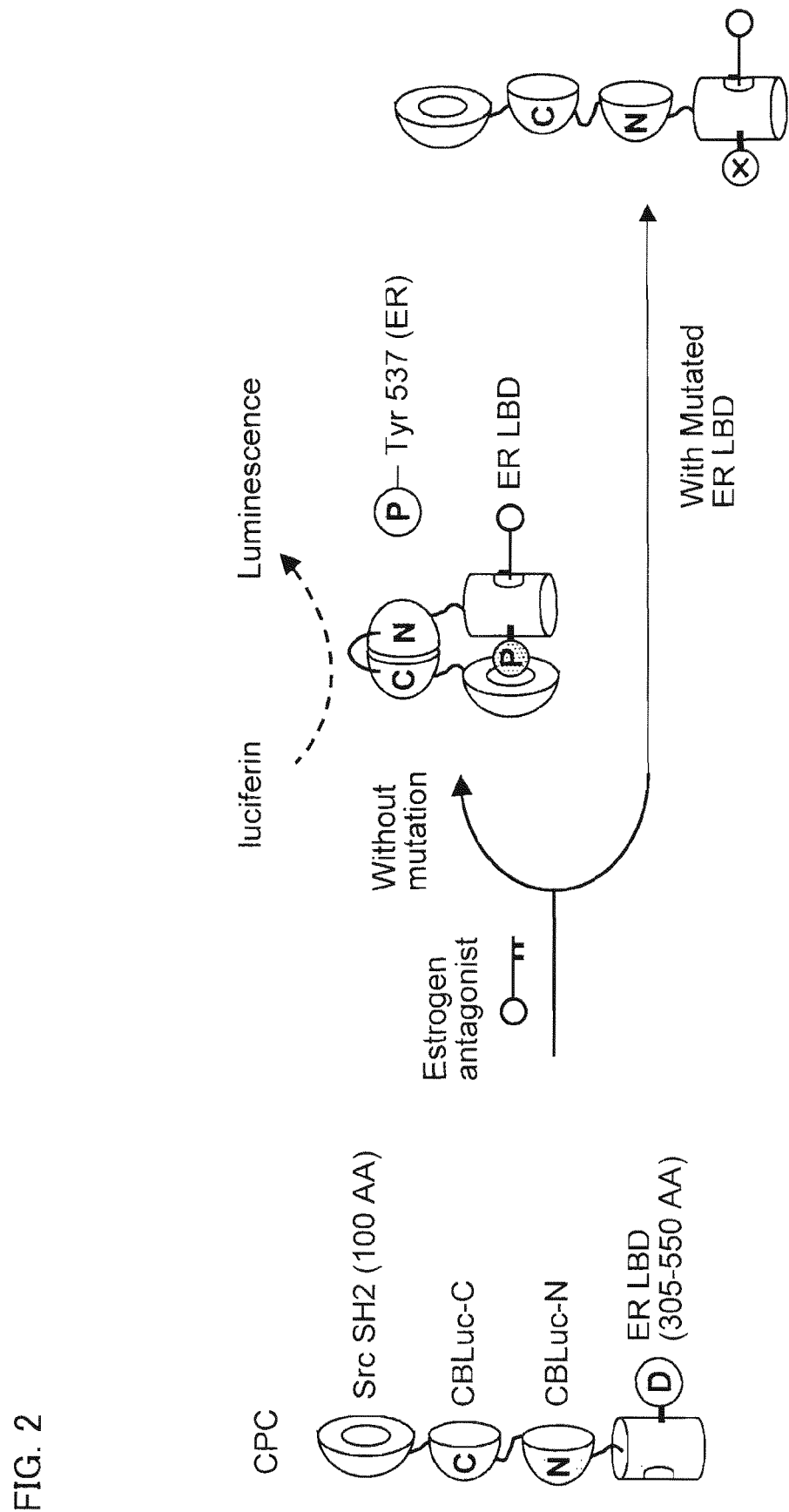
FIG. 2 is a schematic illustrating a ligand recognition mechanism of a bioluminescent probe (CPC) according to the present invention.

FIG. 2 schematically illustrates a ligand recognition mechanism of the luminescent probe arranged in this manner. As illustrated in FIG. 2, if estrogen antagonist coexists with the present luminescent probe, Tyr 537 of LBD is phosphorylated, and Src SH2 recognizes the phosphorylated site. Thus, intramolecular interaction occurs between Src SH2 and the phosphorylated site of LBD, so that the adjacent CBLuc-C and CBLuc-N are approximated to each other and complement. This results in emission of light. Here, in case where Tyr 537 of ER LBD is point-mutated to Phe, ER LBD is not phosphorylated, so that ER LBD and Src SH2 are not bound to each other. Hence, CBLuc-C and CBLuc-N do not complement, so that light is not emitted.

Figure 4:
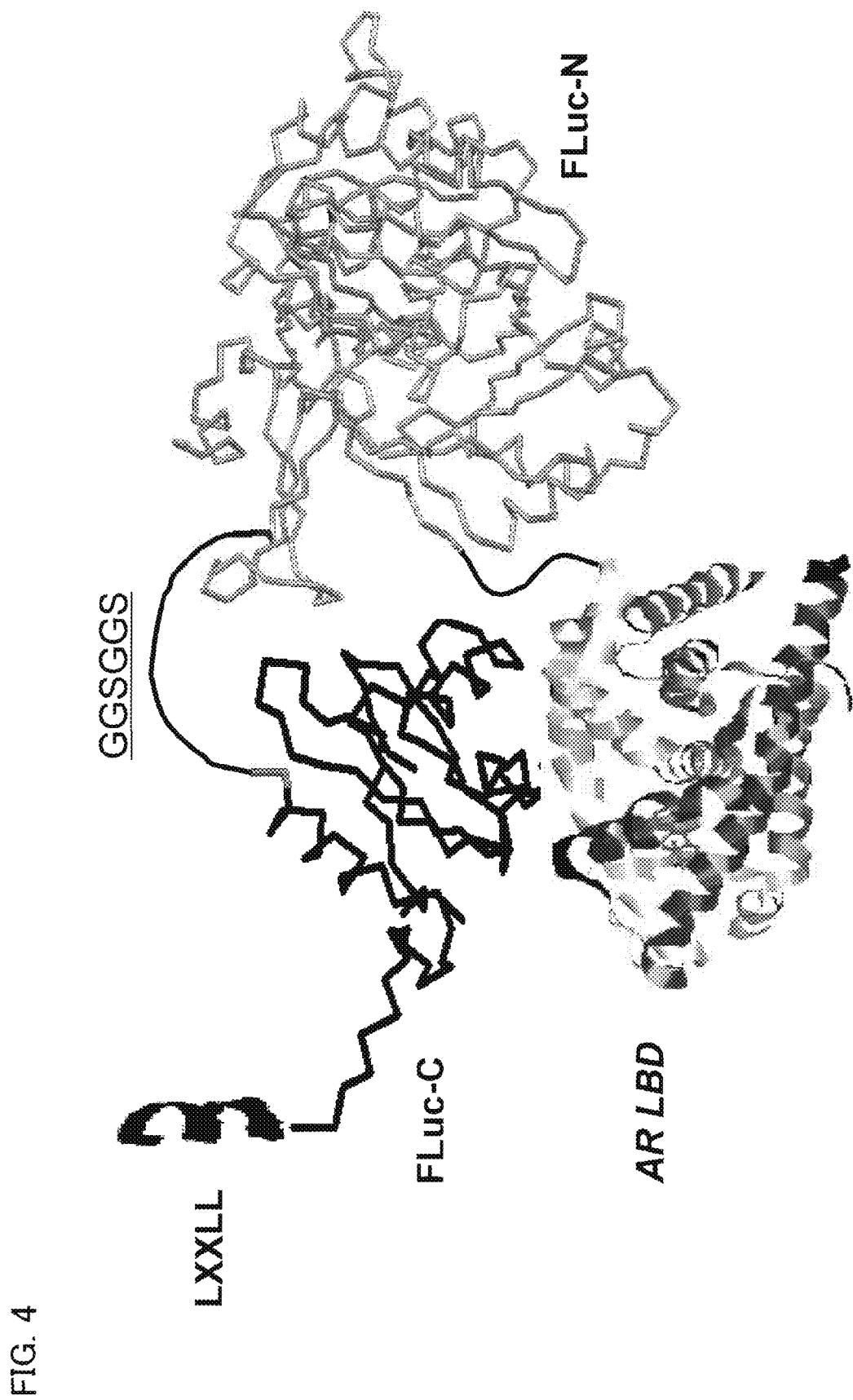
FIG. 4 is a molecular structure of a bioluminescent probe (CPF) according to the present invention which is constructed via expression of pCPF.

In case of using AR LBD as the ligand binding protein and using LXXLL motif as the recognition protein in order to detect androgen, it is preferable that C-LE is linked to the carboxy-terminal of the LXXLL motif and N-LE is linked to the amino-terminal of AR LBD. In this case, it is preferable that FLuc is circularly permutated as the luciferase, and the subsequent C-LE (FLuc-C) of FLuc and N-LE (FLuc-N) of FLuc are tandemly placed in this order. Crystal structures of CBLuc and GLuc have not been reported yet, but a crystal structure of FLuc has been clarified. FIG. 3 illustrates the crystal structure of FLuc. The present luminescent probe is specifically arranged so that LXXLL motif, FLuc-C, FLuc-N, and AR LBD are tandemly linked in this order from the side of the N-terminal. FIG. 4 illustrates an example of conformation of the luminescent probe arranged in this manner.

The luminescent probe according to the present invention may be obtained by linking the component polypeptides, after performing genetic transformation, the chemical synthesis, or a similar method. However, the luminescent probe according to the present invention can be obtained also as follows. The cell is transfected with an expression vector carrying a chimera DNA tandemly linking polynucleotides encoding the component polypeptides, and the vector is expressed in the transfected cell.

Here, the chimera DNA is such that DNA fragments derived from different lineages are tandemly fused, and the chimera DNA expresses a fusion protein in which each polypeptide serves as its components. The chimera DNA according to the present invention consists of tandemly linked polynucleotides which can express a fusion protein serving as a single-molecule-format luminescent probe. In the present specification, "living cell" denotes a cultured cell keeping its original function or a eukaryotic cell (yeast cell, insect cell, animal cell) existing in a living organism, particularly, is a cell derived from a mammal including a human being. The living cell includes also a prokaryotic cell.

In the present specification, the fusion protein can be such that proteins or polypeptides derived from different lineages are artificially linked. In the present specification, the term "polypeptide" can be replaced by "peptide" or "protein". The fusion protein according to the present invention may be chemically synthesized or may be isolated from the natural source. The term "isolated" polypeptide or protein denotes polypeptide or protein picked up from the natural environment. For example, a polypeptide or protein reproduced by recombination in a host cell is considered as being isolated like a natural or recombinant polypeptide or protein substantially purified by any appropriate techniques.

In the luminescent probe according to the present invention, the polypeptides, i.e., the components include: a purified natural product; a product obtained by a chemical synthesis technique; and a product obtained, by a recombinant technique, from a prokaryote or eukaryote host (e.g., bacterial cell, yeast cell, plant cell, insect cell, and mammalian cell).

Further, the luminescent probe according to the present invention may include peptides as an additional component. Examples of the additional peptide include epitope marker peptides such as poly His tag or Myc tag, Flag tag, and the like. In a preferable mode, the fusion protein according to the present invention can be recombined and expressed in a modified manner. For example, an additional amino acid of the fusion protein according to the present invention, particularly, a region of an electrically charged amino acid is improved in stability and durability in the host cell during purification or subsequent manipulation and storage. Thus an addition of a polypeptide to N- or C-terminal of the probe may be beneficial for improving the sensorial performance.

Preferably, the luminescent probe according to the present invention can be a fusion protein consisting of polypeptide specified in any one of SEQ ID Nos: 1 through 3 or a mutant thereof. In the present specification, in case where the term "mutant" used in describing the polypeptide or protein, this term denotes a peptide or protein in which at least one amino acid is point-mutated, is inserted, is reversed, is repeated, is deleted, or is type-substituted in the original amino acid sequence. In case where the recognition protein recognizes the ligand-activated ligand binding protein, the polypeptide or protein alters the luminescence intensity of the luciferase via complementation of the two fragments of the dissected luciferase.

In one embodiment, a mutant of the luminescent probe according to the present invention is preferably a fusion protein which alters the luminescence intensity via complementation of the two fragments of the dissected luciferase in case where the recognition protein recognizes the ligand-activated ligand binding protein, where the fusion protein consists of peptides in which one or several amino acids specified in any one of SEQ ID Nos: 1 through 3 are deleted, substituted, or added.

Such a mutant is generated, for example, via deletion, insertion, reversal, type-substitution, (e.g., substitution of a hydrophilic residue with another residue: Generally, a highly hydrophilic residue is not substituted with a highly hydrophobic residue), and point-mutation.

It is well known in the art that some amino acids in the polypeptide can be easily modified without having any influence on a structure or a function of the polypeptide. Further, it is well known in the art that, among natural proteins, there are not only an artificially modified mutant but also a naturally occurring mutant keeping a structure or function of the protein.

Person skilled in the art can easily mutate one or several amino acids in the amino acid sequence of the polypeptide by using a well known technique. For example, according to a publicly known method for point mutation, it is possible to mutate any base of the polynucleotide encoding the polypeptide. Further, it is possible to produce a deletion mutant or an addition mutant by designing a primer corresponding to a certain site of the polynucleotide encoding the polypeptide. The method described in the present specification can easily determine whether the produced mutant has desired activity or not.

In a preferable mutant, conserved or nonconserved amino acids are substituted, deleted, or added. The mutant is preferable to be made via silent substitution, addition, or deletion. The substitution of conserved amino acids is particularly preferable. These do not alter the intrinsic luminescence activity of the luminescent probe according to the present invention.

Typical examples of the substitution of conserved amino acids are as follows: Aliphatic amino acids Ala, Val, Leu, and Ile can be substituted each other; Amino acids having a hydroxyl residue such as Ser and Thr can be exchanged; Amino acids having an acidic side chain such as Asp and Glu can be exchanged; Amino acids having an amide residue such as Asn and Gln can be substituted; Amino acids having a basic residue such as Lys and Arg can be substituted; and Amino acids having an aromatic residue such as Phe and Tyr can be substituted.

In an embodiment, it is preferable that the luminescent probe according to the present invention is a fusion protein encoded by a polynucleotide consisting of a DNA sequence specified in any one of SEQ ID Nos: 4 through 6 or a mutant of the fusion protein. Here, the mutant is a fusion protein which alters the luminescence intensity of the luciferase via complementation of the two fragments of the dissected luciferase in case where the recognition protein senses that the ligand-activated ligand binding protein, and the fusion protein is encoded by the polynucleotide consisting of DNA oligomers obtained by deleting, substituting, or adding one or several bases out of the base sequences specified in any of SEQ ID Nos: 4 through 6.

In another embodiment, the mutant of the luminescent probe according to the present invention is a fusion protein which alters the luminescence intensity in case where the recognition protein recognizes that the ligand is bound to the ligand binding protein, and the fusion protein is encoded by a polynucleotide hybridizable with a polynucleotide, consisting of DNA oligomers complement with a base sequence specified in any one of SEQ ID Nos: 4 through 6, under a stringent condition.

The hybridization can be performed by a well known method described in Sambrook et al., Molecular Cloning, A Laboratory Manual, 2d Ed., Cold Spring Harbor Laboratory (1989). Generally, higher temperature and lower salt concentration result in higher stringency (it is more difficult to perform hybridization), so that more homologous polynucleotide can be obtained. An appropriate hybridization temperature varies depending on a base sequence and a length of the base sequence. For example, in case of using, as the probe, a DNA fragment consisting of 18 bases encoding six amino acids, the temperature is preferably 50° C. or lower.

In the present specification, the term "stringent (hybridization) condition" denotes a condition under which incubation is performed overnight at 42° C. in a hybridization solution (containing 50% formamide, 5×SSC (150 mM of NaCl, 15 mM of trisodium citrate), 50 mM of sodium phosphate (pH7.6), 5×Denhardt's solution, 10% dextran sulfate, and 20 µg/ml of denatured sheared salmon sperm DNA), and then the resultant is filtered in 0.1×SSC at around 65° C. to be washed. The polynucleotide denotes a polynucleotide (DNA or RNA) hybridized with "a part" of a polynucleotide longer than a reference polynucleotide by at least around 15 nucleotides (nt), more preferably at least around 20 nt, further more preferably at least around 30 nt, still further more preferably around 30 nt or longer.

In another embodiment, the mutant of the luminescent probe according to the present invention is a fusion protein which alters the luminescence intensity via complementation of the two fragments of the dissected luciferase in case where the recognition protein senses that the ligand-activated ligand binding protein, and the fusion protein is encoded by a polynucleotide consisting of a DNA sequence at least 66%, more preferably 80%, 95%, or 99% identical to the DNA sequence specified in any one of SEQ ID Nos: 4 through 6.

If a DNA sequence is over 66% identical to the original DNA sequence, we can generate an identical fusion protein with the DNA sequence because of silent mutation. According to a codon list, for example, a codon encoding valine may be any one of GUU, GUC, GUA, and GUG. Thus, a completely identical fusion protein probe can be produced even if up to 33% of genetic bases are different. Hence, "66%" is a meaningful numeral in determining whether the base sequence is identical or not.

Further, many proteins whose functions have been clarified include naturally occurring mutants or isoforms. Even as estrogen receptor (ER) exemplified in the present embodiment, both ERα and ERβ exist in the nature, and it is known that ERα and ERβ are the same in the binding affinity to estrogen (Non Patent Literature 24). However, it should be noted that homology between the two amino acid sequences is only 30% in the N-terminal domain (NTD) and is only 53% in the ligand binding domain (LBD).

Further, it should be noted that, in glucocorticoid receptor (GR) which is a same nuclear receptor as ER and AR, there are isoforms such as GRαA, GRβA, GRα2, GRβ2, GRAα, GRAβ, GR-P, and GR-βB. The GRs function in vivo as the same GR (Swiss-Prot P04150).

For example, the phrase "polynucleotide consisting of a DNA sequence at least 66% identical to a reference (QUERY) base sequence of a polynucleotide encoding the fusion protein according to the present invention" denotes a condition under which the target DNA sequence may have mismatch of at most 33 nucleotides (bases) out of 100 nucleotides in the reference DNA sequence of the polynucleotide encoding the fusion protein according to the present invention and this is regarded as being identical to the reference DNA sequence. In other words, in order to obtain the polynucleotide consisting of a DNA sequence at least 66% identical to the reference DNA sequence, it is necessary that 33% or less of bases of the reference DNA sequence can be deleted or can be substituted with other bases or many bases corresponding to at most 33% of all the bases of the reference DNA sequence can be inserted into the reference DNA sequence. The mismatch of the reference DNA sequence may occur, in a dispersing manner, at a 5' or 3' terminal site, or at an individual site somewhere in a base of the reference DNA sequence, or at one or more adjacent groups in the reference DNA sequence.

Further, the present invention provides the polynucleotide encoding the luminescent probe according to the present invention. By introducing the polynucleotide according to the present invention into the cell, it is possible to express the luminescent probe according to the present invention in the cell. In one embodiment, it is preferable that the polynucleotide according to the present invention is a polynucleotide consisting of a DNA sequence specified in any one of SEQ ID Nos: 4 through 6 or a mutant of the polynucleotide.

In the present specification, the term "polynucleotide" can be replaced by "gene", "nucleic acid", or "nucleic acid molecule", and denotes a polymer of a nucleotide. In the present specification, the term "DNA sequence" denotes a sequence of deoxyribonucleotide (referred to also as A, G, C, and T) or ribonucleotide (C, A, G, and U). Further, the "polynucleotide containing a base sequence specified in the sequence number 1 or a fragment of the polynucleotide" denotes a polynucleotide containing a sequence specified by deoxynucleoside A, G, C, and/or T of the SEQ ID No: 1 and a fragmentation site of the polynucleotide.

The polynucleotide according to the present invention can exist in a form of RNA (e.g., mRNA) or in a form of DNA (e.g., cDNA or genome DNA). The DNA can be double-stranded or may be single-stranded. The single-stranded DNA or RNA can be a code strand (known also as a sense strand) or can be a non-code strand (known also as an antisense strand).

In one embodiment, it is preferable that the mutant of the polynucleotide according to the present invention encodes the fusion protein which alters the luminescence intensity via complementation of the two fragments of the dissected luciferase in case where the recognition protein senses that the ligand-activated ligand binding protein, and the mutant is any one of the following polynucleotides: a polynucleotide consisting of a DNA sequence in which one or several bases out of the original DNA sequences specified in SEQ ID Nos: 4 through 6 are deleted, substituted, or added; a polynucleotide hybridizable, under a stringent condition, with a polynucleotide consisting of a DNA sequence complementary with the DNA sequence specified in any one of SEQ ID Nos: 4 through 6; and a polynucleotide consisting of a base sequence at least 66%, more preferably at least 80%, 85%, 90%, 92%, 95%, 96%, 97%, 98%, or 99% identical to the original DNA sequence specified in any one of SEQ ID Nos: 4 through 6.

The polynucleotide according to the present invention may include a sequence such as a sequence of an untranslated region (UTR) or a vector sequence (including an expression vector).

A source from which the polynucleotide according to the present invention is obtained is not particularly limited, but it is preferable to use physiological subjects (e.g., organs of a human or a mouse). In the present specification, the term "physiological subjects" denotes a natural source (a tissue sample or a cellular sample obtained from living subjects).

As described in the present specification, the fusion protein expressed from the polynucleotide according to the present invention can be used as a probe for visualizing molecular events inside and outside the cell. More specifically, the fusion protein according to the present invention is constituted as a single-chain fusion protein, and the conformation of the fusion protein changes when the ligand activates the ligand binding protein, and the ligand-activated protein then binds the recognition protein. Further, the N- and C-terminal fragments of the circularly permutated luciferase sandwiched between the ligand binding protein and the recognition protein are approximated and complement each other so as to vary the luminescence intensity. In this manner, dynamics of intercellular molecules, signaling processes, and the like can be visualized and traced by the fusion protein according to the present invention on the basis of a change of the luminescence intensity. Thus, by using the fusion protein according to the present invention, it is possible to detect bioactivity, concentration, and the like of a target ligand with high efficiency. This is useful, for example, in screening of a biological risk factor such as a carcinogen and in quantitative evaluation of pharmacological activities of an anticancer agent (upon screening of a new drug candidate).

That is, the object of the present invention is to provide a highly efficient fusion protein probe encoded by a polynucleotide and is to provide the fusion protein construction method, the polynucleotide synthesis method, and the like, which have been described in detail in the present specification. Thus, it should be noted that also a fusion protein probe encoded by a polynucleotide which may be obtained by a method other than the aforementioned methods fall within the technical scope of the present invention.

[2. Vector]

The present invention also provides a vector for expressing the fusion protein in a living organism or cells. By using the vector according to the present invention, it is possible to transfect the polynucleotide, encoding the fusion protein according to the present invention, into a living organism or cultured cell lines, thereby expressing the fusion protein according to the present invention in the living organism or cells.

The vector according to the present invention is characterized as a gene carrier for the polynucleotide according to the present invention. The vector according to the present invention is not particularly limited as long as the polynucleotide according to the present invention is included. An example of the vector is a recombinant expression vector or the like in which cDNA of the polynucleotide according to the present invention is subcloned. A method for constructing the recombinant expression vector is not particularly limited, but a method using plasmid, phage, cosmid, or the like may be adopted.

A specific type of the vector is not particularly limited, and a vector which can express the fusion protein in a host organism can be appropriately selected. Further, in the vector according to the present invention, a publicly known tissue-specific promoter sequence may be incorporated to control expression of the polynucleotide according to the present invention (e.g., expression in a specific tissue of a living organism). That is, in order to indeed express the polynucleotide according to the present invention, a promoter sequence is appropriately selected, and the thus selected promoter sequence and the polynucleotide according to the present invention can be subcloned into various types of plasmid or the like, thereby using the resultant vector as the expression vector. Further, it is possible to selectively introduce the present probe into a specific organ by using a known vector which selectively resides in a specific organ.

The vector according to the present invention can be introduced into a host organism by a publicly known method such as a microinjection method, an electroporation method, or the like. Alternatively, it is possible to adopt an intracellular introduction method using lipid (BioPORTER (Gene Therapy Systems), Chariot (Active Motif), or a similar method. The host cells is not particularly limited, and it is possible to favorably use conventionally known various types of cells, living organism, or the like.

Note that, the target fusion protein according to the present invention does not have to be constitutively synthesized but may be transiently expressed by adding IPTG. Further, the vector may include a sequence in which a tag sequence such as polyhistidine tag, HA tag, Myc tag, Flag tag, or the like is added to any of N- and C-termini of the synthesized protein.

It is preferable that the vector according to the present invention includes at least one selection marker. Examples of such a marker include: dihydrofolate reductase or drug-resistant genes such as neomycin, Zeocin, Geneticin, Blastcidin S, Hygromycin B, and the like in cultivation of eukaryote; and drug-resistant genes such as kanamycin, Zeocin, actinomycin D, cefotaxime, streptomycin, carbenicillin, puromycin, tetracycline, or ampicillin, in cultivation of *Escherichia coli* and other bacterium. By using the selection marker, it is possible to confirm whether the polynucleotide has been transfected into the host cells or not and to further confirm whether the polynucleotide is indeed expressing proteins in the host or not.

By using the vector according to the present invention, it is possible to introduce the fusion protein according to the present invention into a living organism or culture cell lines, thereby expressing the fusion protein according to the present invention in the living organism or culture cell lines. Further, by using the vector according to the present invention in a cell-free protein synthesis system, it is possible to synthesize the fusion protein in vitro according to the present invention.

It can be said that the vector according to the present invention needs to include the polynucleotide encoding the fusion protein according to the present invention in this manner. That is, it should be noted that also a vector other than the expression vector falls within the technical scope of the present invention.

[3. Transmformant]

The present invention provides a transformant which can express the fusion protein according to the present invention. The transformant according to the present invention is characterized by including the polynucleotide according to the present invention and the vector carrying the polynucleotide. In the present specification, the term "transformant" denotes not only a cell, a tissue, or an organ, but also a living organism. The transformant according to the present invention is not particularly limited as long as the transformant includes the polynucleotide according to the present invention and the vector carrying the polynucleotide.

The transformant according to the present invention can be obtained by introducing the polynucleotide according to the present invention or the recombinant expression vector including the polynucleotide into a living organism or culture cell lines so that the fusion protein according to the present invention can be expressed.

A method for introducing the polynucleotide according to the present invention or the vector including the polynucleotide into the host, that is, a transfection method is not particularly limited, and it is possible to favorably adopt conventionally known methods such as electroporation, calcium phosphate method, liposome method, DEAE dextran method, and the like. Further, the transformant according to the present invention may be a transient transformant in which the polynucleotide according to the present invention is transiently expressed without being incorporated into a genome or may be a constitutive transformant in which the polynucleotide according to the present invention is incorporated into a genome and is permanently expresses the fusion protein.

By using the transformant according to the present invention, it is possible to express the fusion protein according to the present invention. Thus, it is possible to evaluate properties, activity, and the like of a ligand through its stimulation to the transformant according to the present invention and monitoring variances of the luminescence intensity of the transformant.

[4. Ligand Detection Method and Ligand Detection Kit]

The present invention further provides a ligand detection method for determining a ligand in a subject sample using a ligand detection kit. The ligand detection method according to the present invention is characterized by including the procedure of incubating the subject sample with the fusion protein according to the present invention. In the present invention, a substrate for the enzyme incorporated in the fusion protein may be added to the subject sample in an appropriate. This makes it possible to detect the ligand in the subject sample in accordance with the luminescence intensity of the fusion protein according to the present invention. In the present specification, the "subject sample" may be a ligand or may be a sample containing a ligand. Further, the subject sample may be a physiological subject in a cell in which the fusion protein according to the present invention is expressed.

In the foregoing step, when the luminescence intensity of the fusion protein according to the present invention changes in the presence or absence of the subject sample, it is possible to detect, in the subject sample, a ligand bound to the ligand binding protein fused in the fusion protein according to the present invention. As shown in below-described Examples, the ligand detection method according to the present invention can determine properties, activity, concentration, and the like of the ligand.

The ligand detection method according to the present invention can detect an unknown antagonist on the basis of an already known agonist. For example, the subject sample containing an antagonist candidate is first brought into contact with the fusion protein according to the present invention, and the already known agonist is additionally brought into contact with the fusion protein, to monitor the luminescence intensity of the fusion protein according to the present invention. If the candidate substance of the subject sample acts as an antagonist, the candidate substance occupies an agonist binding site of the ligand binding protein, so that a subsequently introduced agonist cannot be bound to the ligand binding protein as a result of the competition.

In the ligand detection method according to the present invention, typically, a living cell transfected with an expression vector carrying a polynucleotide encoding the fusion protein according to the present invention is stimulated the subject sample to monitor the subsequent luminescence intensity variance before and after the stimulation. A method for bringing the fusion protein according to the present invention into contact with the subject sample is not particularly limited, but it may be so arranged that the subject sample is added to a culture medium of the living cell in which the fusion protein according to the present invention is expressed and a stimulate in the subject sample passes by the plasma membrane via endocytosis so as to be in contact with the fusion protein. In case where the subject sample is an intracellular substance, it may be so arranged that the fusion protein according to the present invention is expressed in the cell so as to be in contact with the subject sample. Even in a cell-free condition, by using culture liquid secreted in the culture medium containing the fusion protein according to the present invention or using a purified fusion protein according to the present invention, substrates of luciferases can be easily incorporated, thereby performing measurement in vitro.

In the ligand detection method according to the present invention, it is possible to adopt the following methods in case of using the luminescent probe expressed in the living cell. However, these are not restrictive.

(i) A plasmid carrying a polynucleotide encoding the fusion protein according to the present invention is transfected into a living cell on a 24-well plate and is further incubated for 16 hours.

(ii) The cell is saturated with a substrate solution.

(iii) The cell is stimulated by the subject sample and the consequent variances of the luminescence intensity before and after the stimulation are measured with a luminometer.

In the ligand detection method according to the present invention, it is possible to adopt the following methods in case of performing experiment in vitro using the fusion protein according to the present invention, but these are not restrictive.

(i) A luminescent probe purified by a publicly known method is mounted on the end of a cross-shaped paper piece whose diameter is 1.2 cm and is then dried.

(ii) 15 mL of a substrate solution containing a stimulator is dropped on the center of the cross-shaped paper piece and the luminescence intensity thereof is immediately measured with a luminescence scanner (e.g., RAS-3000; FujiFilm).

The ligand detection kit according to the present invention for detecting a ligand is characterized by including the fusion protein according to the present invention. Further, the present kit may further include a substrate of a luciferase contained in the fusion protein according to the present invention.

Here, the fusion protein according to the present invention which is included in the present kit can be expressed in eukaryotic and prokaryotic cells cultured in a large scale. For example, in case of using mammalian cells, a large amount of conventionally and publicly known secretion signal peptide are cofused to the probe backbone and secreted in the culture medium, thereby obtaining a culture supernatant containing a large amount of luminescent probes. The culture supernatant can be used in an assay without being subjected to the purification step. Further, by adding a purification tag (e.g., His Tag), it is possible to easily purify a large amount of fusion proteins.

As in the thus obtained kit including the fusion protein, also a kit including a transformant expressing the fusion protein according to the present invention can be used to detect a ligand in a subject sample. Further, a kit including the polynucleotide according to the present invention and a cell which can be transfected with the polynucleotide and a kit including the vector according to the present invention and a cell which can be transfected with the vector can be used to detect a ligand in the subject sample likewise.

[5. Probe Construction Method and a Probe Construction Kit]

The present invention further provides a method for constructing the probe according to the present invention and a kit comprising the probe. The probe construction method according to the present invention is characterized by including the step of transfecting a cell with the polynucleotide according to the present invention or the vector according to the present invention. In the present method, a cell is transfected with the polynucleotide according to the present invention or the vector according to the present invention, and the probe according to the present invention is expressed in the cell, thereby constructing the probe according to the present invention. The probe expressed in the cell can be harvested and purified from the cell on the basis of a publicly known method.

Specifically, after the cell is transfected and cultured by using the polynucleotide or the expression vector according to the present invention, the probe according to the present invention can be harvested and purified from the culture or the like by a generally adopted technique (e.g., filtration, centrifugation, fracture of cell, gel filtration chromatography, ion exchange chromatography, or the like). Further, in case where the purification tag is added to the polynucleotide expressed in the cell, the probe can be more easily harvested.

The probe formation kit according to the present invention is characterized by including the polynucleotide according to the present invention and the vector according to the present invention. Further, the present kit may further include a cell transfected with the polynucleotide according to the present invention or the vector according to the present invention. Further, the present kit may include a substrate for a luciferase fused in the polypeptide according to the present invention. Further, the probe construction kit according to the present invention may include ribonucleic acid encoding the fusion protein according to the present invention.

The probe according to the present invention can be constructed, for example, as follows. First, an enzyme is dissected into two fragments, i.e., C- and N-terminal fragments. Further, a circularly permutated C- and N-terminal fragment are tandemly linked and sandwiched between the ligand binding protein and the recognition protein. The probe according to the present invention may be constructed in this manner.

The fusion protein according to the present invention makes it possible to suppress the background luminescence intensities down to 1/1000 and to greatly enhance the signal-to-noise ratio. Thus, it is possible to visualize and detect various protein-protein interactions with a high efficiency.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

Example 1

Plasmid Construction

The respective cDNA fragments consisting of circularly permutated probes were generated by the polymerase chain reaction (PCR) to introduce each unique restriction site at each end of the fragments using adequate primers and templates. For example, a plasmid carrying Yellow Cameleon-3.1 (YC3.1) donated by Dr. Miyawaki was utilized for amplifying *Xenopus laevis* calmodulin (CaM) in PCR as a template (see Non Patent Literature 4). The specific restriction enzyme recognition sites were summarized in FIG. 5.

Figure 5:
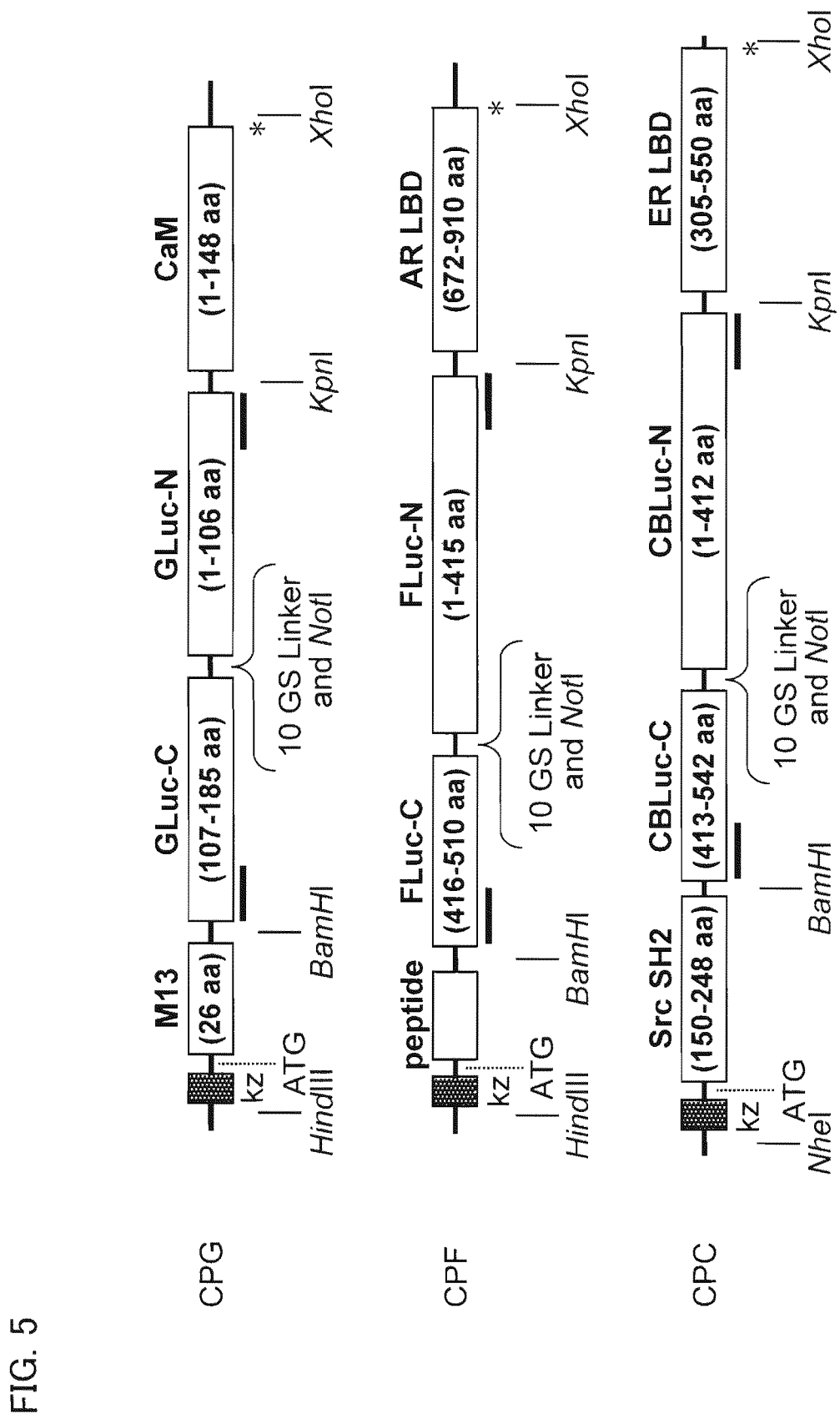
FIG. 5 is a conceptual diagram illustrating bioluminescent probes each containing circularly permutated luciferases according to the present invention.

The restricted cDNA fragments were then ligated as shown in FIG. 5 and subcloned into the pcDNA 3.1(+) (Invitrogen). The plasmids were respectively named pCPC (cpCBLuc probe), pCPF (cpFLuc probe), and pCPG (cpGLuc probe), according to the kind of the luciferases circularly permutated in the probes. The probes expressed in the plasmids may be called CPC, CPF, CPG, respectively.

Figure 14:
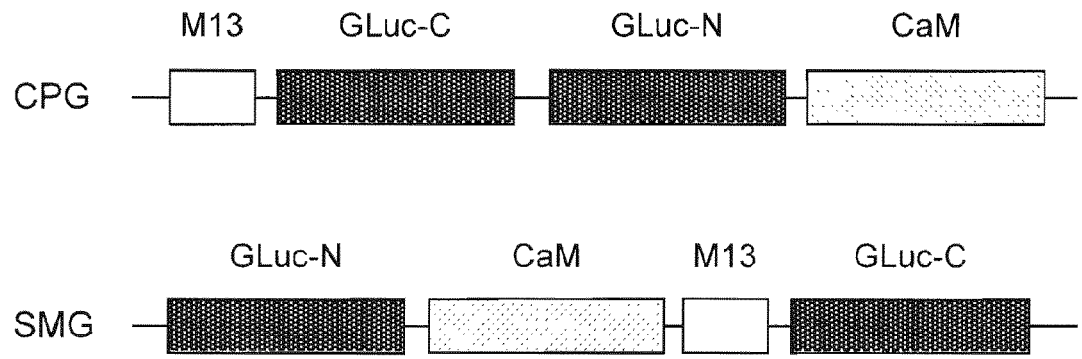
FIG. 14 is a schematic comparison of the molecular structures of CPG and SMG.

In addition, the cDNA of ligand binding domain of estrogen receptor (ER LBD) in pCPC was point-mutated at Y537 from TAT to TTT: i.e., Y537F. This plasmid was named pCPC-mutant. As another control of the present cpCPC probe, a conventional single-molecule-format probe was parallelly constructed as animated in FIG. 9. The plasmid was named pSMC. As a control of cpGLuc probe (CPG), a single-molecule-format probe SMG was made as shown in FIG. 14. This plasmid was named pSMG.

All the plasmids constructed for the present study were sequenced to ensure fidelity with a BigDye Terminator Cycle Sequencing kit and a genetic analyzer ABI Prism310 (Applied Biosystems).

Here, in order to generate rational fragments used in the circular permutation of the luciferase inserted into each plasmid, the present inventors studied, as follows, a dissection site at which the luciferase is dissected so that bioluminescent is recovered via an intramolecular complementation. The present inventors have studied several dissection sites at which the luciferase is dissected so that the activity is temporarily lost and is immediately recovered (Non Patent Literatures 11 and 17). The present inventors studied the dissection site on the basis of hydrophilicity distribution assays on all the amino acid sequences of GLuc, FLuc, and CBLuc.

Figure 6:
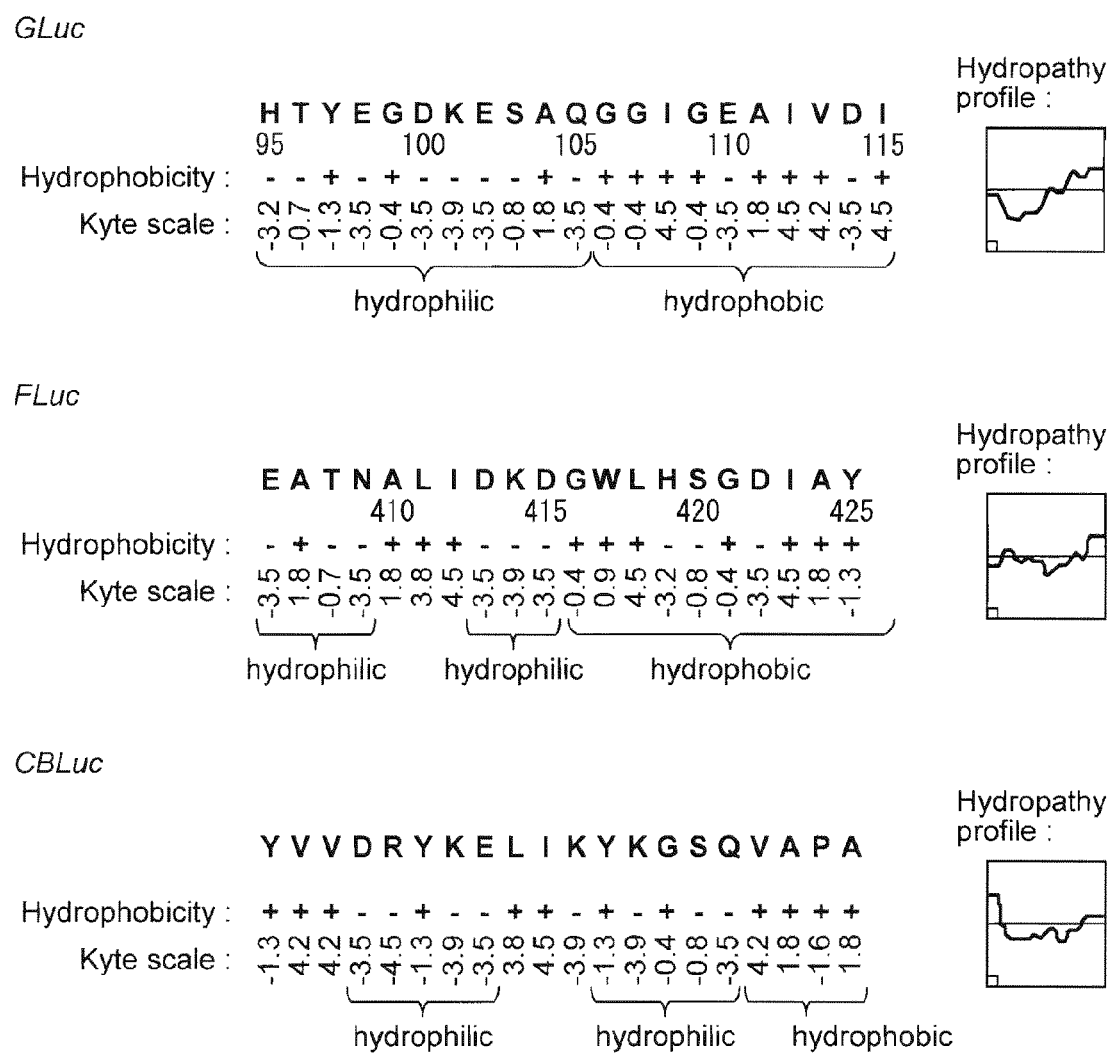
FIG. 6 is a diagram illustrating results of hydrophilicity search on GLuc, FLuc, and CBLuc.

FIG. 6 shows results of the hydrophilicity distribution assays on the luciferases. On the basis of the studies having been performed by the present inventors, they consider that a hydrophilic region in the amino acid sequence may exist between two main domains constituting the luciferase. With a focus on the hydrophilic region, the present inventors studied the dissection site. As a result, they found it optimal that GLuc is dissected at between 106 and 107, and FLuc is dissected at between 415 and 416, and CBLuc is dissected at between 412 and 413, and each of them is circularly permutated to construct the probe. The original N- and C-termini of the luciferase are gene-fused with 10GS linker, and a new terminal is provided on the dissection site, thereby performing circular permutation.

Example 2

Cell Culture and Transfection

COS-7 cells derived from African green monkey kidney were raised on a 24-well plate with Dulbecco's modified eagle's medium (DMEM; Sigma) supplemented with 10% steroid-free fetal bovine serum (FBS) and 1% penicillin-streptomycin (P/S) at 37° C. in a cell incubator maintaining 5% $CO_2$ (Sanyo). The COS-7 cells were transiently transfected with pCFG, pCPF, or pCPC (0.2 μg per each well) using a plasmid transfection reagent, TransIT-LT1 (Mirus). The cells were extensively incubated in the 5% $CO_2$ incubator for 16 hours.

Example 3

Comparison of Relative Luminescence Intensities by CPC, CPF, or CPG

Figure 7:
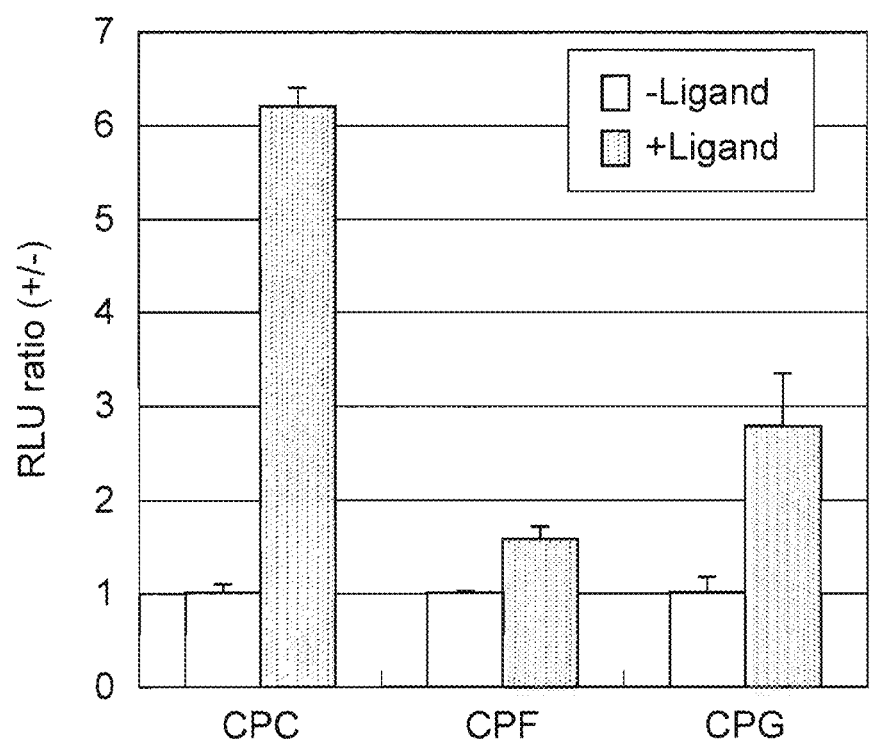
FIG. 7 is a graph comparing ligand affinities of bioluminescent probes according to the present invention.

The relative luminescence intensities by CPC, CPF, or CPG were compared in the presence or absence of the ligand. The results are shown in FIG. 7.

First, the COS-7 cells carrying pCPC or pCPF were stimulated with $10^{-6}$ M of 4-hydroxy tamoxifen (OHT) or 5α-dihydroxytestosterone (DHT) (final concentration). The luminescence intensities were developed with a Bright-Glo substrate solution (Promega), and integrated for 15 seconds with a luminometer (Minilumat LB9506; Berthold). The brief procedure for the use of the Bright-Glo substrate solution is as follows.

The mammalian cells were washed once with PBS 20 minutes after stimulation with ligand. A 40 μL of the substrate (D-luciferin) solution was added to each well of the plates. Three minutes after substrate addition, the plate was tapped gently, and the subsequent cell lysates were transferred to a test tube for determining the luminescence intensities.

On the other hand, the cells carrying pCPG were harvested by trypsinization and centrifugation. The cells were gently mixed with a 40 μL substrate (coelenterazine) solution containing 1 mM histamine or PBS. The luminescence intensities were then determined with the luminometer (Minilumat LB9506). The results thereof are as follows.

The results represented that CPC and CPG respectively produced 6- and 3-times stronger luminescence than background, whereas the CPF exhibited poor signal-to-background ratios. These data show that (i) luciferases can be circularly permutated for constructing bioluminescent probes, (ii) intramolecular protein complementation between CP fragments of luciferases indeed occurs upon presence of a ligand, (iii) the recovered luminescence intensities are strong enough to be utilized for molecular imaging, (iv) the variances in the signal-to-noise ratios may be caused by steric hindrance and spatial mismatch among the components in a CP probe.

Example 4

Comparison of the Luminescence Intensities by CPC or CPC-Mutant

CBLuc or its mutant produces highly tissue-transparent red luminescence at 615 nm with insensitivity to pH, temperature, and heavy metal ions. The present inventors made use of these merits of CBLuc Red in synthesizing a new probe. Upon stimulation of ER ligands, Y537 in ER LBD is phosphorylated. This is sensitively recognized by SH2 domain of Src (Non Patent Literature 18). The present inventors made use of this typical nongenomic interactions of ER with Src in building up the present CP probe.

The present inventors examined with CPC and CPC-mutant whether the phosphorylation of ER LBD at Y537 motivates intramolecular interaction between SH2 domain of Src and ER LBD. As in Example 2, COS-7 cells raised on a 24-well plate were transiently transfected with pCPC or pCPC-mutant. Sixteen hours after transfection, the cells were then stimulated with various ligands ($10^{-6}$ M) for 20 minutes. The ligands were as follows: vehicle (0.1% DMSO; final concentration), OHT (4-hydroxytamoxifen), estrone, 17β-estradiol ($E_2$), DHT (5α-dihydrotestosterone), and cortisol.

The luminescence intensities were measured as follows. Transfected COS-7 cells were incubated for 16 hours in a cell incubator. The cells were lysed with 200 μL of a cell lysis buffer carrying D-luciferin, and the whole lysates were transferred into a quartz cell (45×12.5×7.5 mm). The light emission in the range from 400 to 700 nm was recorded (n=3) with a luminescence spectrophotometer (FP-750; Jasco). The spectrum by CPC was compared with CPC-mutant in the presence or absence of a ligand. The results of the comparison are shown in FIG. 8.

Figure 8:
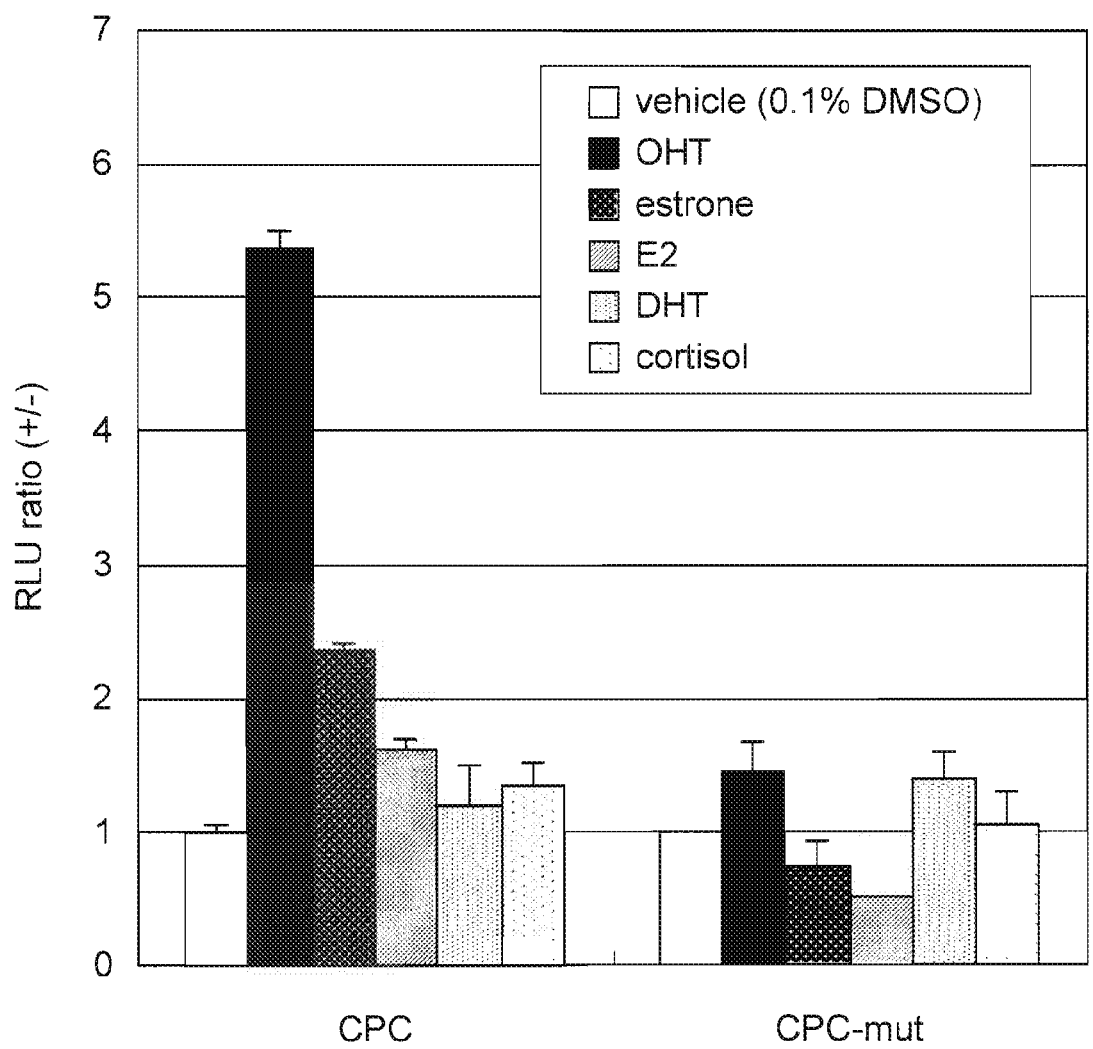
FIG. 8 is a graph showing ligand affinities of CPC and CPC-mutant based on the interaction between ER LBD and Src SH2.

As illustrated in FIG. 8, CPC recognized various steroids and was especially sensitive to an estrogen antagonist, OHT, whereas, CPC-mutant was insensitive (did not react) to all the ligands. The results show that (i) the intramolecular interactions occurs via phosphorylation of ER LBD at Y537, (ii) Y537 in ER is phosphorylated ligand-dependently, (iii) the luminescence intensities by CPC can index antagonistic activities of ligands, (iv) in an analytical point of view, signal-to-noise ratios are large enough to discriminating nongenomic activities of ligands. It was previously debated whether $E_2$ exerts phosphorylation of ER at Y537. The present experiment supports that not only $E_2$, but also OHT can induce phosphorylation of ER at Y537. Although both $E_2$ and OHT phosphorylate ER LBD, OHT induces more favorable conformation change of ER LBD in the recovery of CBLuc activity than $E_2$. This observation is correspondent with a previous luciferase study on ER antagonists.

Example 5

Dose-Response Curves of CPC to Ligands and the Comparison with SMC

Ligand sensitivity of CPC in COS-7 cells were examined with varying concentrations of steroids. As in Example 2, COS-7 cells raised on 24-well plates were transiently transfected with pCPC. Sixteen hours after transfection, the cells were stimulated with varying concentrations of ligands. The developed luminescence intensities were recorded with the luminometer (Minilumat LB9506). The ligands were as follows: vehicle (0.1% DMSO; final concentration), OHT, estrone, 17β-estradiol ($E_2$), DHT, and cortisol.

Figure 9:
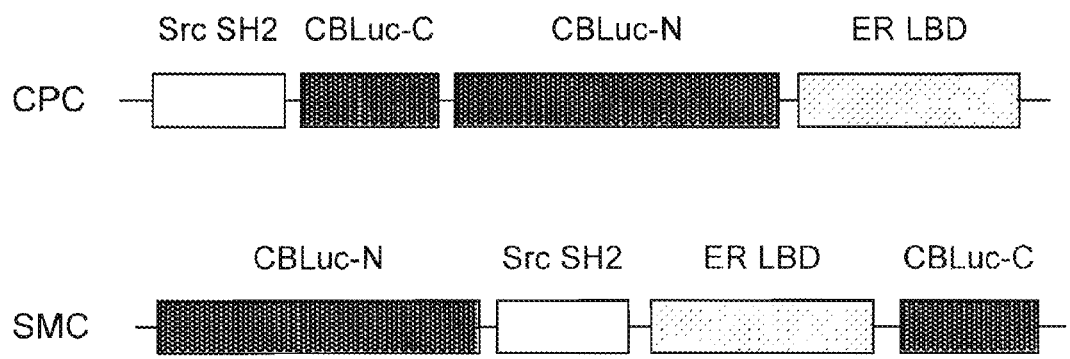
FIG. 9 is a schematic comparison of the molecular structures of CPC and SMC.

As a control of CPC, the sensitivity of SMC shown in FIG. 9 was parallelly examined with the same experimental condition as CPC. As shown in FIG. 9, SMC is different from CPC in that Src SH2 and ER LBD are linked between N- and C-terminal fragments. That is, the luciferases in SMC are not circularly permutated. COS-7 cells were transfected with plasmid pSMC containing SMC. The COS-7 cells were stimulated with varying concentrations of OHT, and the resulting luminescence intensities were determined with the luminometer (Minilumat LB9506).

Figure 10:
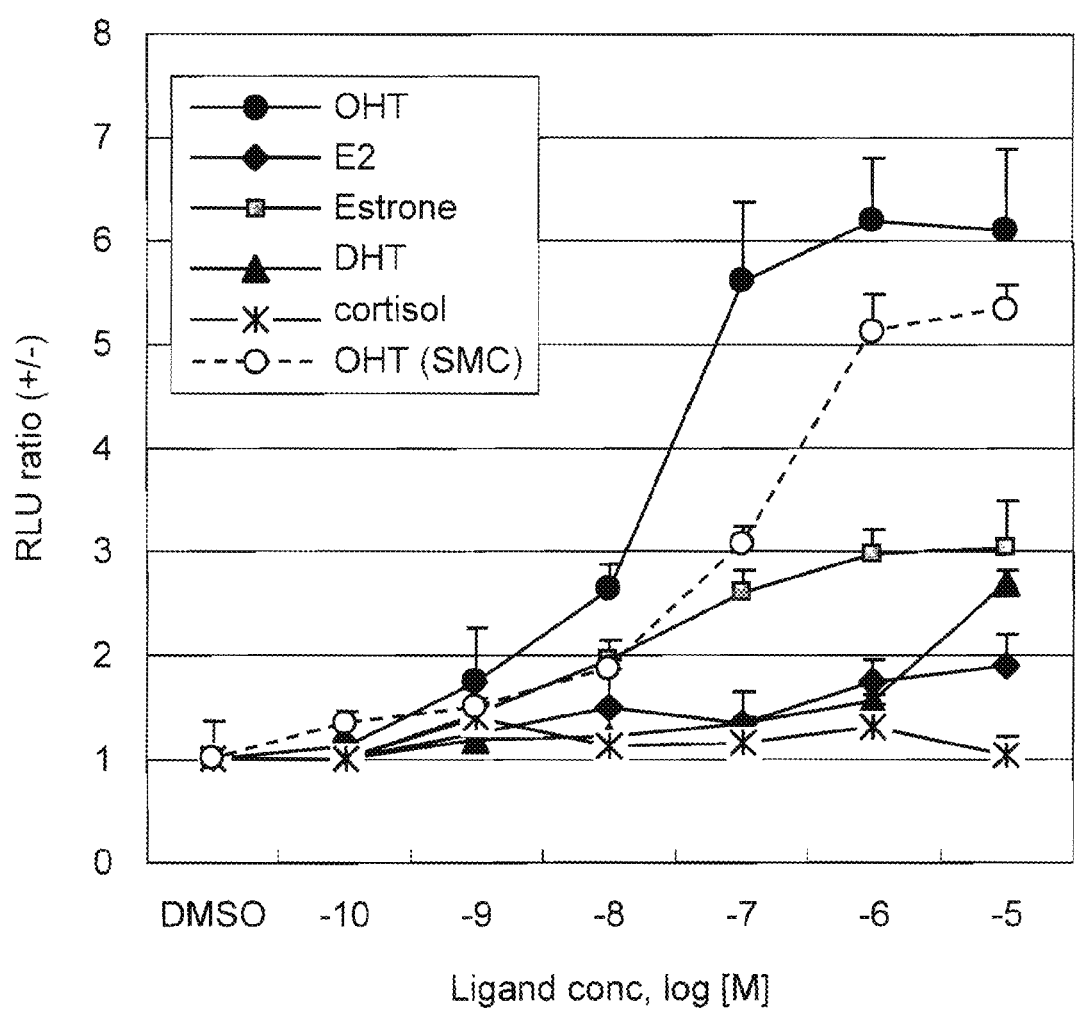
FIG. 10 is dose-response curves of CPC to ligands.

FIG. 10 shows the dose-response curves of CPC and SMC to ligands. As shown in FIG. 10, CPC selectively sensed OHT and even responded to $10^{-9}$ M OHT. The half-maximal effective concentration ($EC_{50}$) was ca. $5 \times 10^{-8}$ M. This is 10 times enhanced sensitivity to a control probe without CP (SMC). SMC emitted seven times stronger background luminescence than CPC: i.e., 38459 vs. 5484 RLU (n=3). The reason of the enhanced detection limit is explained that CP of cpCBLuc favors in the decrease of basal interactions between ER LBD and SH2 in the absence of a ligand.

Example 6

Comparison of Inhibitory Effects of $E_2$ to Antagonist-Bound CPC

On the basis of the result that CPC is sensitive to ER antagonists, not to the agonists, the inhibitory effects of $E_2$ to antagonist binding CPC were examined. As in Example 2, COS-7 cells raised on 24-well plates were transiently transfected with pCPC. Sixteen hours after transfection, the cells were prestimulated with $10^{-5}$ M $E_2$ for 5 minutes. The cells were additionally incubated with one of the following nuclear receptor antagonists ($10^{-6}$ M; final concentration): ciglitazone, ICI182780, genistein, OHT. The resulting luminescence intensities were compared with those from the cells stimulated with an antagonist alone. The results are shown in FIG. 11.

Figure 11:
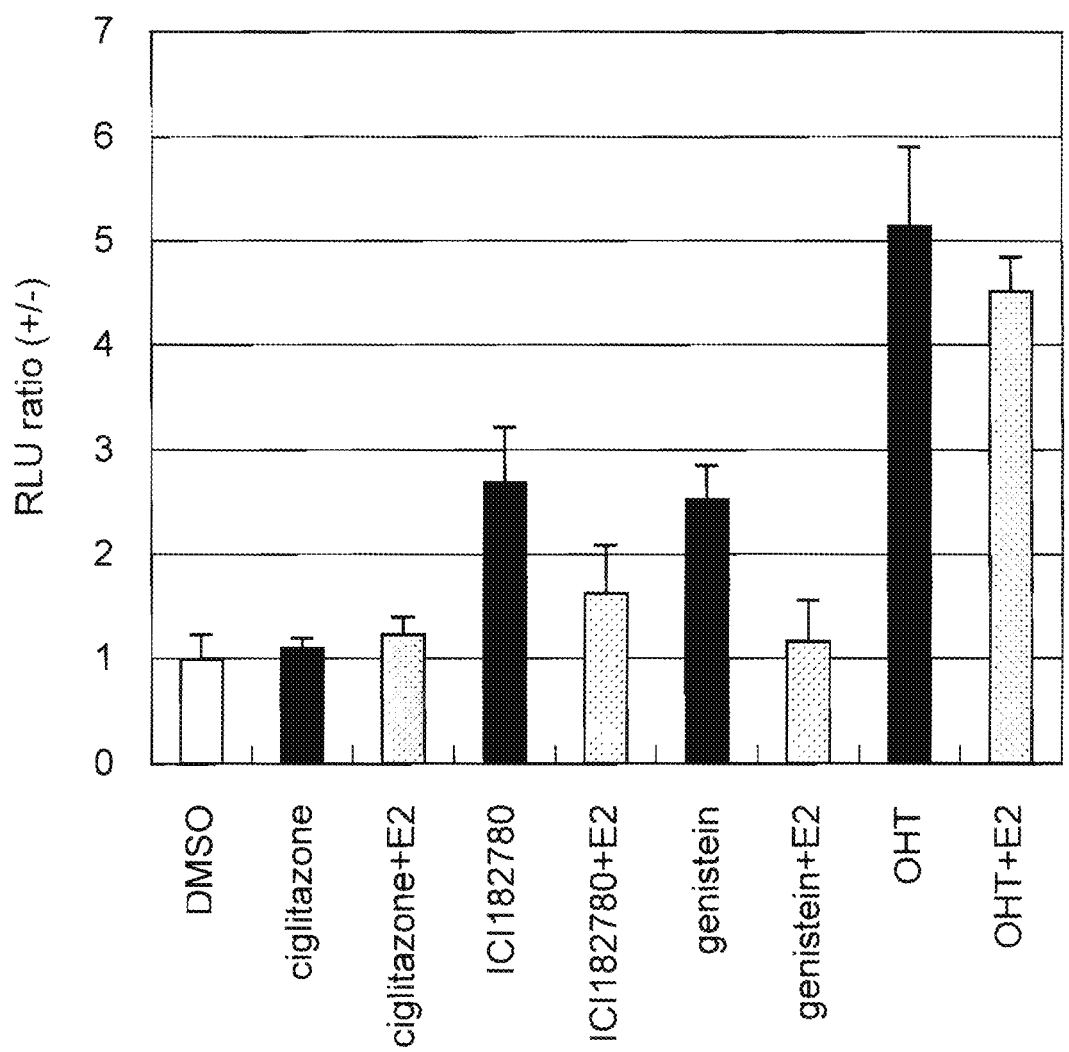
FIG. 11 is a graph comparing relative affinities of CPC to various antagonists.

As shown in FIG. 11, $E_2$ negatively contributed to the luminescence intensities developed by antagonists. The results show that (i) antagonists compete with $E_2$ in binding ER LBD, and (ii) OHT is the most efficient antagonist barely influenced by a 10 times excess of $E_2$.

Example 7

Kinetics of Ligand-Probe Binding

The kinetic aspects of ligand-probe binding were estimated with COS-7 cells carrying pCPC. As in Example 2, COS-7 cells cultured on 12-well plates were transiently transfected with pCPC, and incubated for another 6 hours. The luminescence intensities were recorded at 2, 5, 10, 20, and 30 minutes after addition of $10^{-6}$ M OHT or vehicle (0.1% DMSO). The results are shown in FIG. 12.

Figure 12:
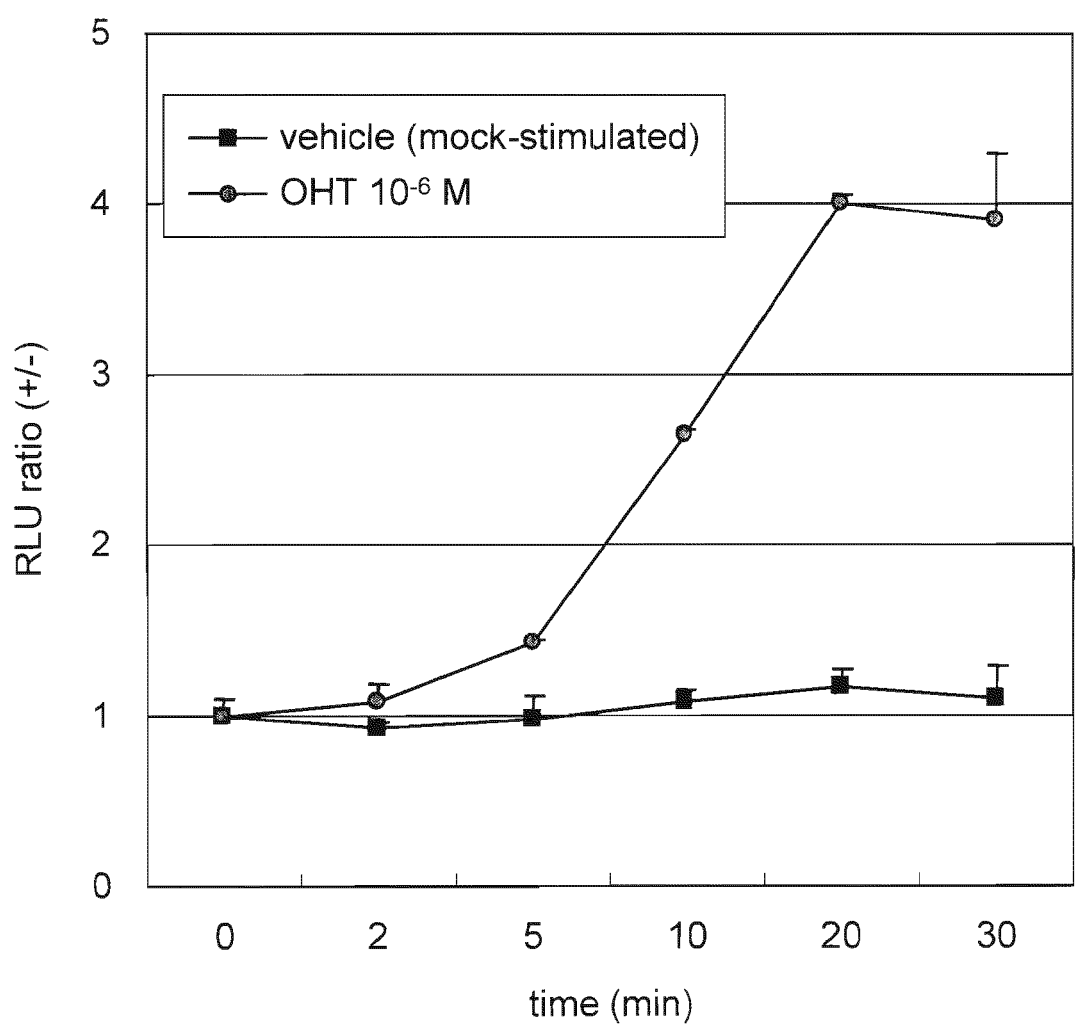
FIG. 12 is a time-course of the luminescent intensities reconstituted by an OHT-CPC interaction.

As shown in FIG. 12, the luminescence intensities by CPC were largely enhanced from 5 minutes after OHT addition, and reached to a plateau in 20 minutes. The total response time, 20 minutes, comprises all the time for (i) penetration of OHT across the plasma membrane, (ii) OHT-ER LBD binding and conformation change of ER LBD, (iii) subsequent binding of ER LBD with Src SH2, and (iv) intramolecular complementation between fragments of CBLuc. It is previously proven with cell-free assays that net ligand-ER binding and conformation change of ER are completed within one minute (Non Patent Literature 19). Therefore, it is considered that large portion of the total response time, 20 minutes, was consumed during the penetration of OHT into the cytosol. This response time is considerably slower than those shown by the present inventor's previous probes. Hydrophilicity of OHT compared to other steroids may cause the late plasma membrane penetration.

Figure 13:
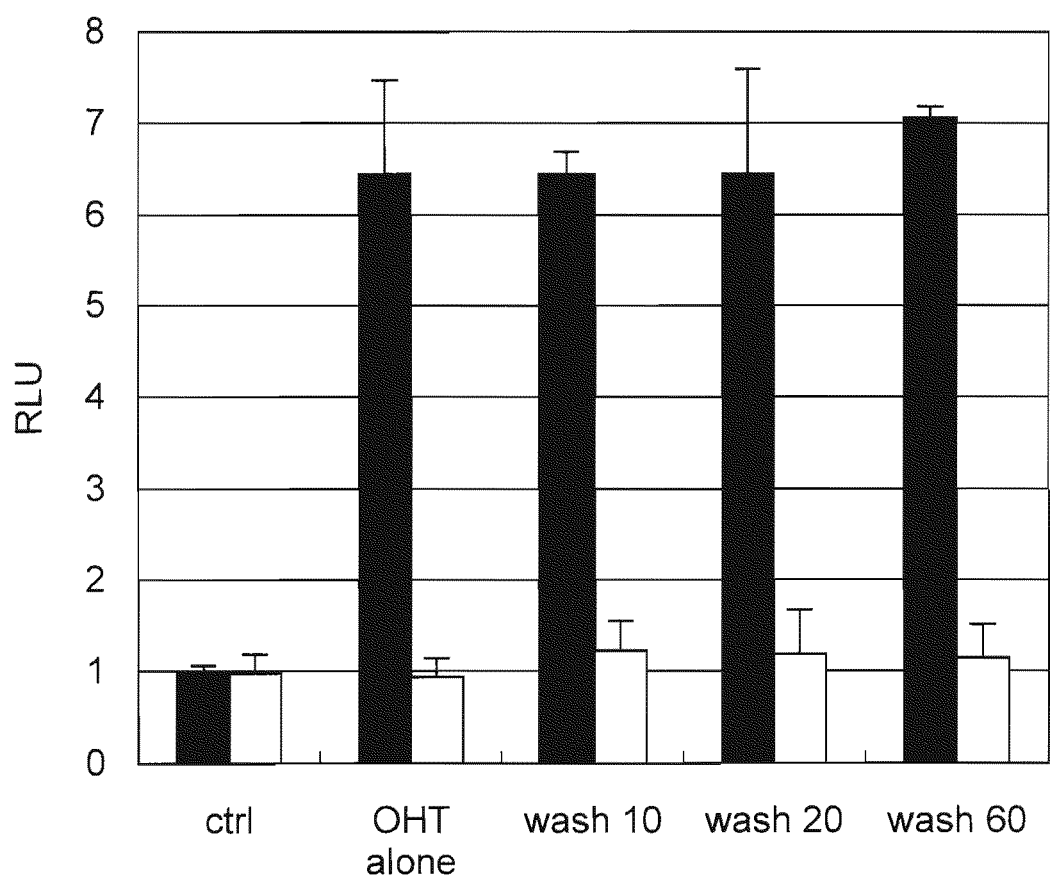
FIG. 13 is the luminescence variances showing a wash-out effect after stimulation of CPC with OHT.

Relaxation of the OHT-CPC binding by time was examined with refreshing the culture medium after OHT stimulation. The cells carrying pCPC were stimulated with $10^{-6}$ M OHT or vehicle (0.1% DMSO) for 20 minutes, and the culture media were then replaced with fresh, ligand-free media. The luminescence intensities at 10, 20, 60 minutes after medium replacement were developed with a Bright-Glo substrate solution. The intensities at each time period were compared with those from the cells mock-stimulated with the vehicle (0.1% DMSO). The results are shown in FIG. 13. In FIG. 13, each black bar chart represents luminescence intensity from the cell stimulated by OHT and each white bar chart represents luminescence intensity from the cell mock-stimulated with the vehicle.

As shown in FIG. 13, the luminescence intensities within 1 hour after medium change were not decreased considerably. Even wash-out after 60 minutes did not weaken the luminescence intensities from the cells. This results may be influenced by one or both of the following reasons: (i) hydrophilicity of OHT postponed the outflux of OHT from the cells, (ii) OHT-triggered Src SH2-ER binding can be endured for a quite long time. Role of helix 12 in ER in this binding may be plausible considering (a) Y537 is located at the start of helix 12 of ER 20, and is recognized by Src SH2 (Non Patent Literature 20), and (b) is at the right place potentially blocking the dissociation of SH2-ER binding. It is interesting to compare the ligand-sensing mechanisms between ER and AR related with the current issue. In physiological circumstances, AR is recycled after transcription, whereas ER is retained in the nucleus after ligand-ER binding (Non Patent Literatures 21 and 22). Namely, ER is decomposed in the nucleus and needs not to release ligand after transcription. These physiological differences in ligand-sensing mechanisms of ER and AR may appear in the sustaining of SH2-ER binding.

Example 8

Determination of the $Ca^{2+}$ Dynamics in COS-7 Cells Transfected with pCPG

The dynamics of cytosolic $Ca^{2+}$ in COS-7 cells were monitored in the cells transfected with pCPG and in the cells transfected with SMG shown in FIG. 14 as a control. The free $Ca^{2+}$ was a representative second messenger in living mammalian cells. As shown in FIG. 14, GLuc was dissected at Q105, and the fragments were circularly permutated with a 10 GS linker. The outer terminals were respectively fused with M13 peptide and calmodulin. SMG is different from CPG in that calmodulin and M13 peptide are linked between N- and C-terminal fragments. That is, the luciferases are not circularly permutated in SMG.

As in Example 2, COS-7 cells cultured in a black, glass-bottom plate (24-well) were transfected with pCPG or pSMG, and stocked in a cell incubator for 16 hours. The cells were saturated with a 300 μL Hank's balanced salt solution (HBSS) buffer containing coelenterazine. The luminescence variances were monitored with a bioluminescence plate reader (Mithras LB 940; Berthold) every 30 seconds before and after addition of histamine ranged from 0.1 to 1 mM. The results are shown in FIG. 15.

Figure 15:
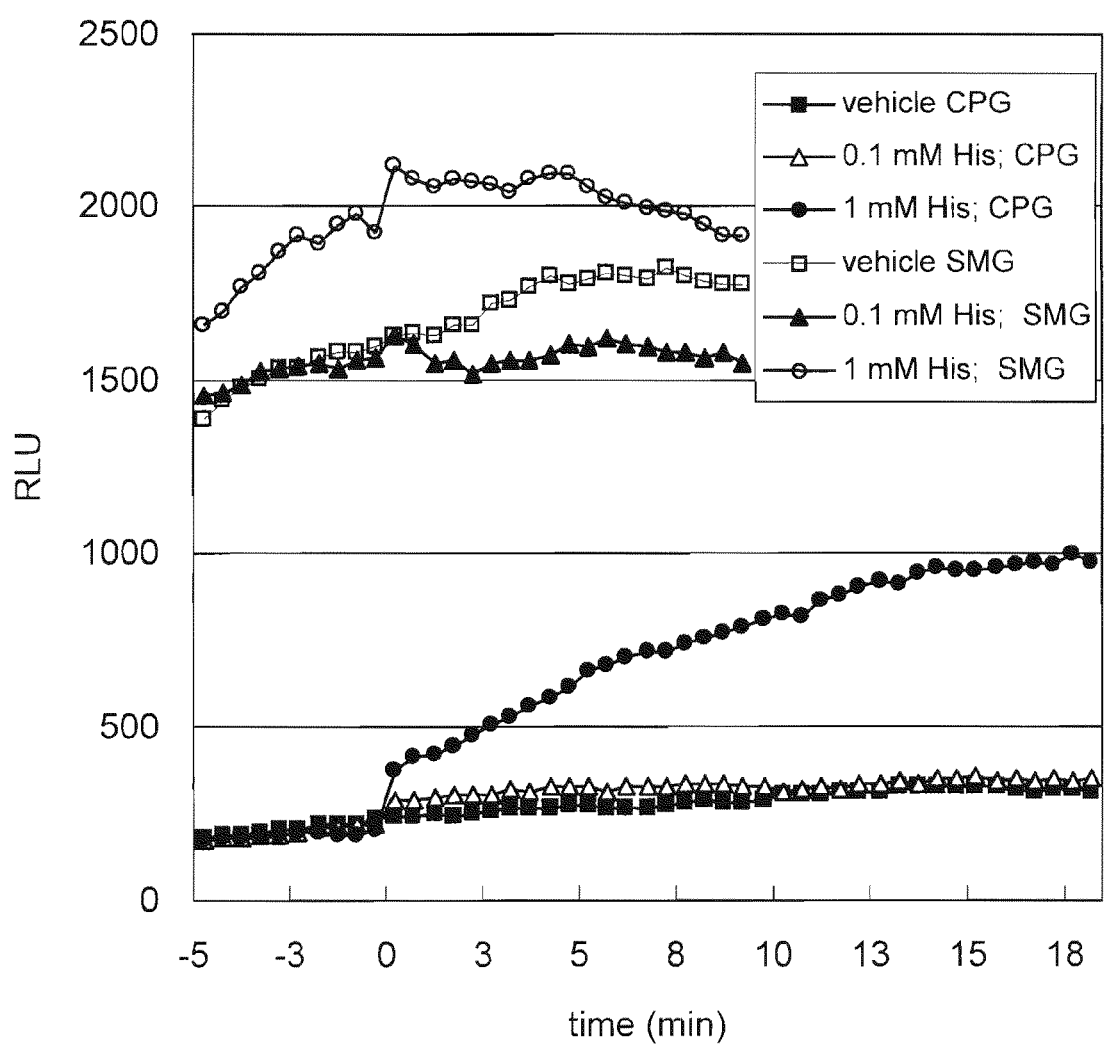
FIG. 15 is a comparison of ligand sensitivities of CPG and SMG before and after ligand addition.

As shown in FIG. 15, in response to 1 mM histamine, CPG quickly increased the luminescence intensities, which approximately reached to a plateau in 10 minutes. On the other hand, SMG exhibited a very high background intensity even in the absence of histamine. Stimulation with 1 mM histamine seldom lifted the luminescence intensities. These results conclude that circular permutation of GLuc favors the decrease of background intensities just like the case where CBLuc is circularly permutated. The decreased basal luminescence enabled us to more easily and more surely determine dynamics of free $Ca^{2+}$ levels triggered by histamine.

Conventionally, real-time imaging of dynamics of second messengers has heavily depended on fluorescence resonance energy transfer (FRET) (Non Patent Literatures 3, 4, and 23). FRET phenomenon between GFP variants can be detectable with a fluorescence microscope. However, only few cells can be observed in the method under autofluorescence. Considering the present CPG provides a simple whole-cell assay and real-time imaging, it is advantageous for tracing molecular dynamics in mammalian cells. This is the first example that histamine-triggered dynamics of a second messenger was determined with a bioluminescent probe in living cells.

Example 9

Retention of $Ca^{2+}$ Levels After Wash-Out, that was Elevated by Various Ligands Retention of cytosolic calcium $Ca^{2+}$ levels in response to an external stimulus were monitored on the basis of the luminescence intensities from COS-7 cells carrying pCPG. As in Example 2, COS-7 cells raised on a 24-well plate were transiently transfected with pCPG, and extensively incubated for 16 hours. The cells were stimulated with the following ligands for 20 minutes: (i) vehicle (PBS), (ii) 0.5 mM histamine, (iii) 0.5 mM histamine plus 10 μM cycloheptadine, (iv) 0.5 mM histamine plus 1 mM thapsigagen, (v) 0.5 mM ATP, (vi) 0.5 mM ATP plus 10 mM cycloheptadine, (vii) 0.5 mM ATP plus 1 mM thapsigagen, (viii) 2 μM ionomycin.

The cells were washed twice with PBS after ligand stimulation, and harvested by trypsinization and centrifugation. This wash-out terminates the external stimulation of ligands for elevating cytosolic $Ca^{2+}$ levels. The cells were resuspended with a 40 mL substrate buffer carrying coelenterazine, and then transferred to a test tube to determine the luminescence with a luminometer (Minilumat LB9506). The results are shown in FIG. 16.

Figure 16:
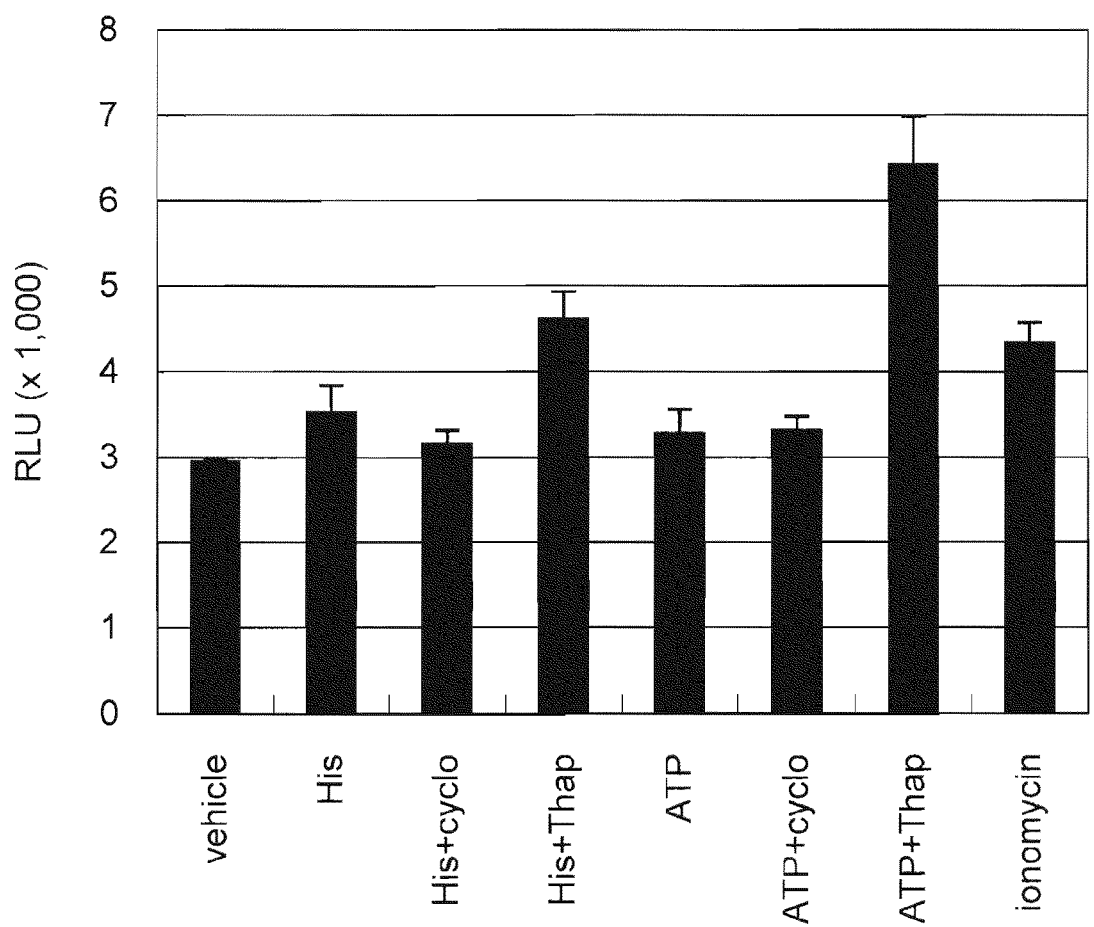
FIG. 16 is a graph showing a wash-out effect (ligand removal) on endogenous $Ca^{2+}$ level, which is elevated by ligand-stimulation to COS-7 cells carrying pCPG.

The resulting luminescence intensities shown in FIG. 16 are interpreted as follows: Because histamine and ATP cannot pass the plasma membrane, they bind their specific receptors on the membrane. The elevated cytosolic $Ca^{2+}$ levels by histamine or ATP alone are quickly decreased by $Ca^{2+}$ pumping of the cells. Additional supplementation of thapsigargin known as an endoplasmic reticulum $Ca^{2+}$ pump inhibitor retained the luminescence intensities elevated by histamine or ATP.

On the other hand, costimulation of cyproheptadine in addition of histamine selective blocked the elevation of cytosolic $Ca^{2+}$ levels. It is considered because cyproheptadine blocked histamine effects as an anti-histamine. Ionomycin triggers influx of exogenous $Ca^{2+}$ into the cytosol. It was resulted in retaining certain levels of $Ca^{2+}$ in the cytosol in spite of the $Ca^{2+}$ pump.

These results show that (i) the present CPG provides a suitable measure for exploring the molecular phenomena in living mammalian cells, and (ii) dynamics of second messengers including $Ca^{2+}$ in living cells can be illuminated with a bioluminescent probe, which was not conducted with a bioluminescent probe, but frequent with a fluorescent measure.

Example 10

Comparison of CPC and its Control (CPC-Ctrl) in Ligand Affinity

Figure 17:
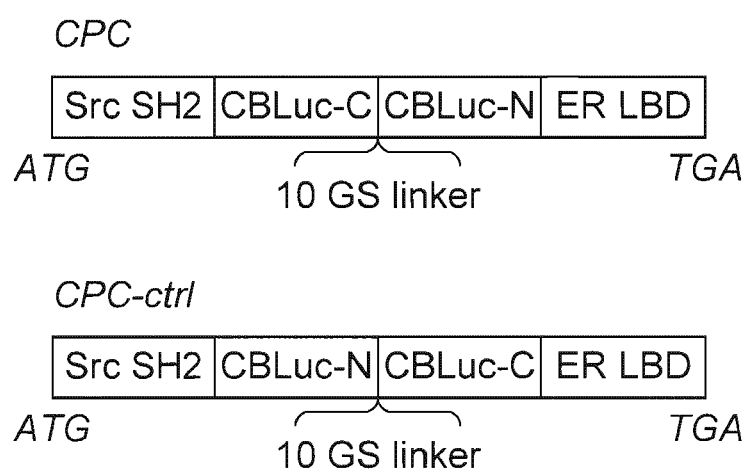
FIG. 17 is a schematic comparison of the molecular structures of CPC and CPC-ctrl.

In the ligand affinity, CPC-ctrl which is another control of CPC was compared with CPC. As shown in FIG. 17, CPC-ctrl is such that N- and C-terminal fragments of CBLuc are linked between Src SH2 and ER LBD in this order. That is, CPC-ctrl is different from CPC only in that an enzyme between Src SH2 and ER LBD is not circularly permutated.

As in Example 2, COS-7 cells cultured on a 24-well plate were transiently transfected with pCPC or pCPC-ctrl. 16 hours after the transfection, the cells were stimulated with $E_2$ or OHT with varying concentrations for 20 minutes. The luminescence intensities were determined with a luminometer. The results are shown in FIG. 18.

Figure 18:
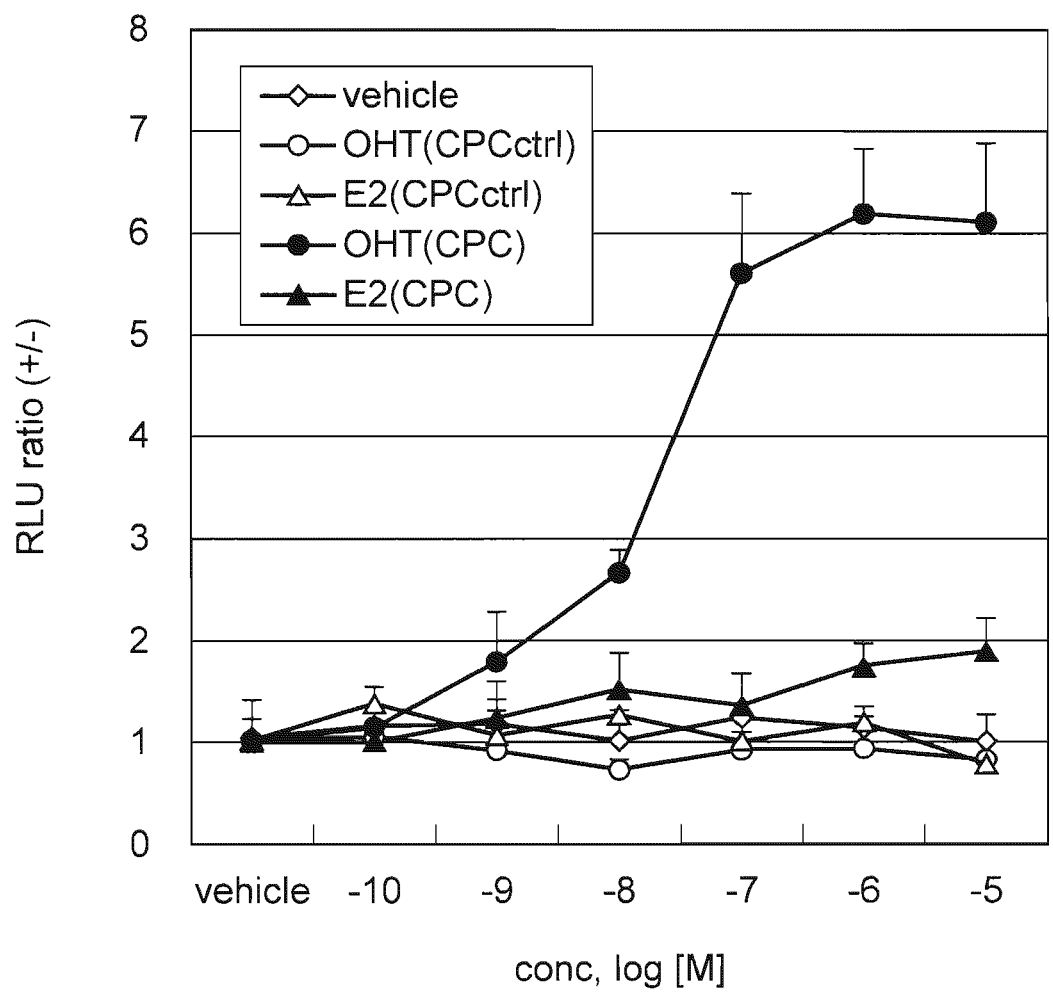
FIG. 18 is a comparison of the luminescence intensities from CPC and CPC-ctrl in response to varying concentration of ligands.

As shown in FIG. 18, CPC selectively sensed OHT and even responded to $10^{-9}$ M OHT. The half-maximal effective concentration ($EC_{50}$) was ca. $5 \times 10^{-8}$ M. On the other hand, there was no variances in the luminescence intensities from CPC-ctrl to OHT or $E_2$ (FIG. 18). The reason thereof is explained that the background luminescence intensities were extremely high even in the absence of a stimulus substance. The background luminescence intensities of CPC-ctrl were around 1000 times greater than the background luminescence intensities of CPC. As a result, a signal-to-background ratio was poor as shown in FIG. 18.

Example 11

Wavelength of Light Emitted from COS-7 Cells Carrying pCPC

With band pass filters shielding light, luminescence wavelengths of the COS-7 cells having pCPC were compared. As in Example 2, COS-7 cells cultured on a 24-well glass plate were transiently transfected with pCPC and were incubated for 16 hours. The cells were saturated with 500 µL HBSS buffer containing coelenterazine and any one of vehicle (0.1% DMSO), $10^{-6}$ M $E_2$ and $10^{-6}$ M OHT. Within 20 minutes after the ligand stimulation, the luminescence intensities from the cells were observed with a series of band pass filters in every predetermined time periods at 510±10 nm, 535±10 nm, 540±10 nm, 560±10 nm, and 610±10 nm. The results are shown in FIG. 19.

Figure 19:
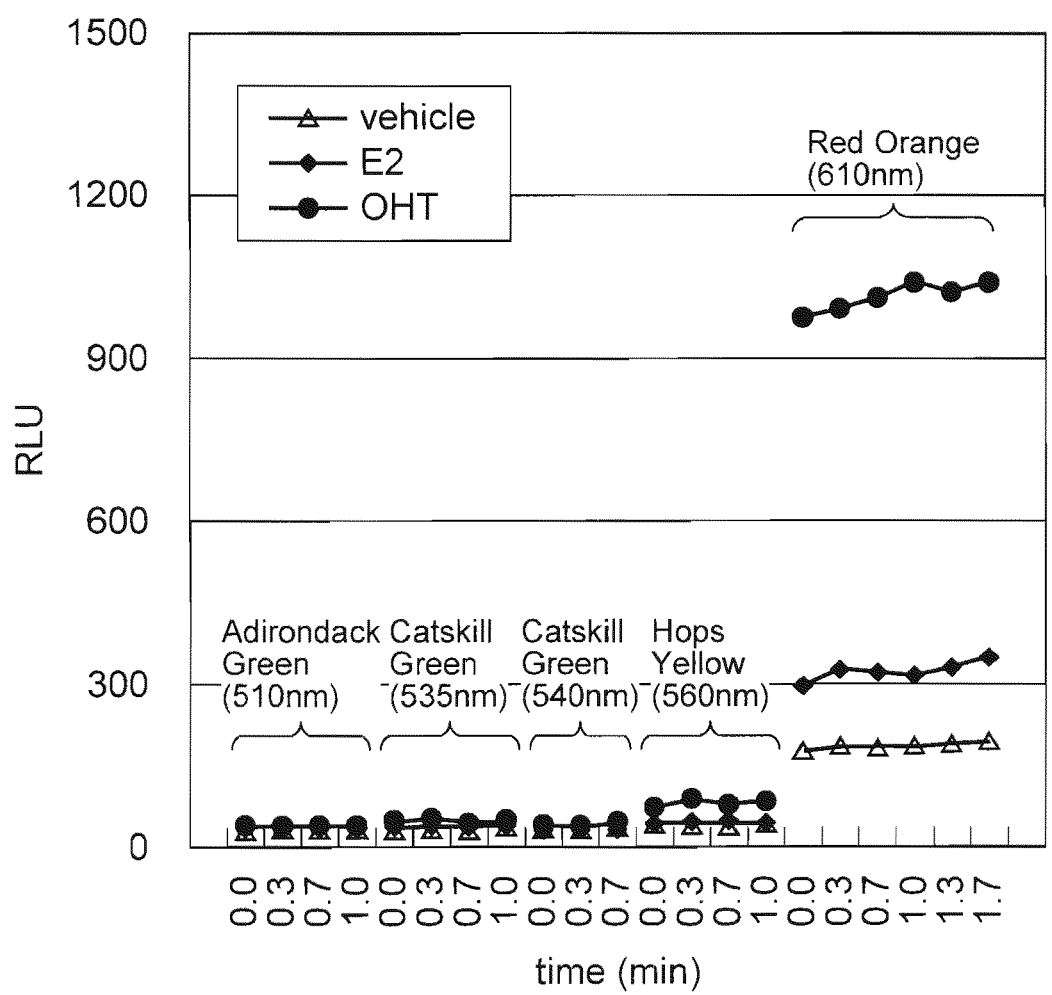
FIG. 19 is a comparison of the luminescence intensities from CPC, passed by various band-pass filters.

As shown in FIG. 19, light from the COS-7 cells efficiently passed the 610±10 nm filter. This shows that the COS-7 cells emitted red-orange light. The luminescence intensities induced by OHT were around 5 times as higher than those induced by the vehicle (0.1% DMSO). On the other hand, the luminescence intensities induced by $E_2$ are higher than those induced by the vehicle, and a difference between them was around 1.8 times. These results show that OHT selectively lifts red-orange light, so that the luminescence intensity can specifically index antagonist activity of the ligand bound to the estrogen receptor.

Example 12

Ligand Affinity of CPG

Figure 20:
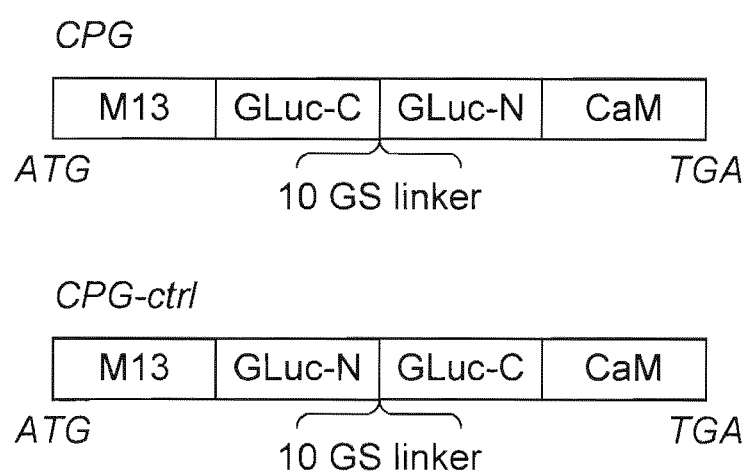
FIG. 20 is a schematic comparison of the molecular structures of CPG and CPG-ctrl.

In COS-7 cells, dynamics of cytoplasm $Ca^{2+}$ were observed with CPG and CPG-ctrl. First, GLuc was dissected at Q105, and the original N- and C-terminals of the fragments were circularly permutated with a 10 GS linker. The outer terminals were respectively fused with M13 and CaM to form CPG. CPG-ctrl which is different from CPG only in that GLuc was not circularly permutated was parallelly formed as a control probe of CPG by the use of the same components as CPG (FIG. 20).

As in Example 2, COS-7 cells cultured in a black, glass-bottom plate (24-well) were transiently transfected with pCPG or pCPG-ctrl, and stocked in a cell incubator for 16 hours. The cells were saturated with a 300 µL HBSS buffer containing coelenterazine. The luminescence variances were monitored with a bioluminescence plate reader (Mithras LB 940; Berthold) every 30 seconds before and after addition of histamine ranged from 0.1 to 1 mM. The results are shown in FIG. 21.

Figure 21:
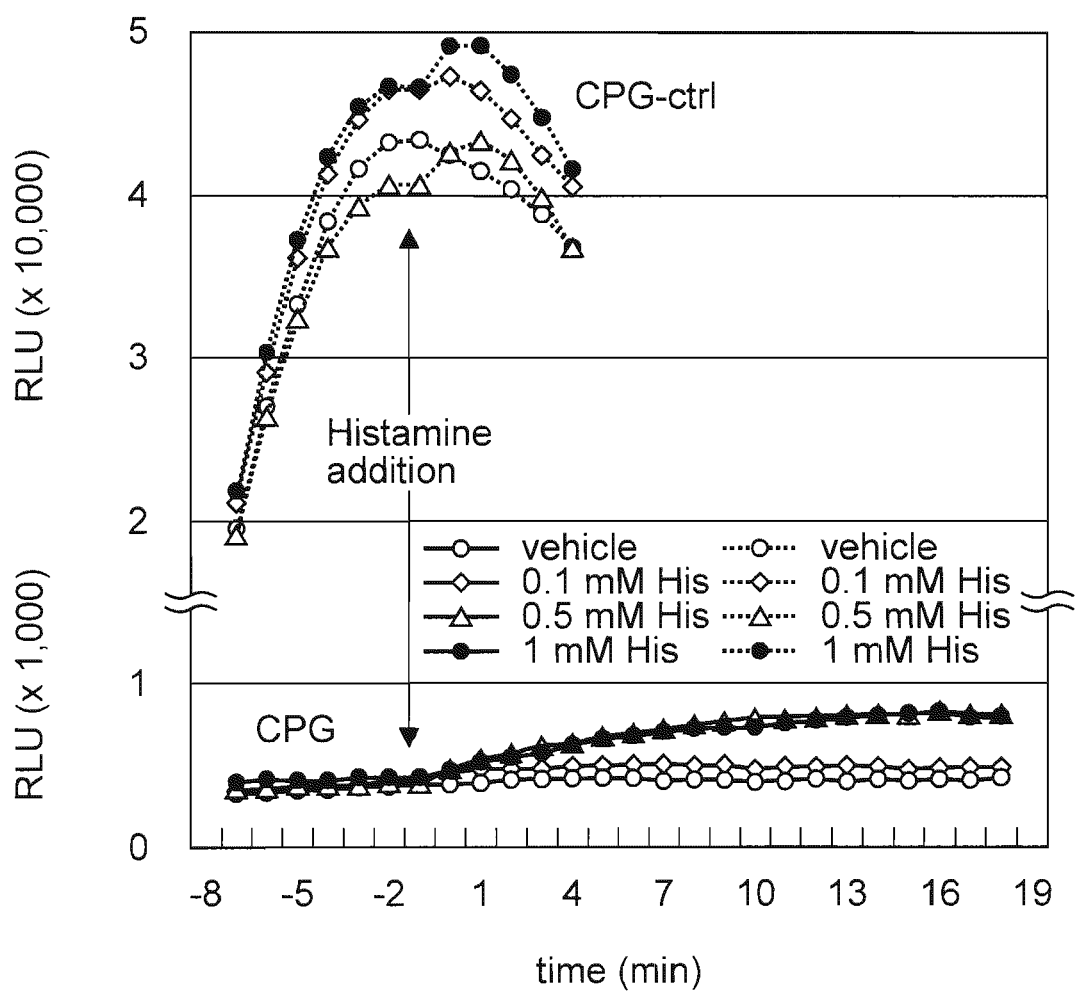
FIG. 21 is a time-course of the bioluminescent intensities from CPG and CPG-ctrl before and after ligand stimulation.

As shown in FIG. 21, in response to 1 mM histamine, CPG quickly increased the luminescence intensities, which approximately reached to a plateau in 10 minutes. CPG started sensing histamine from its 0.25 mM, and the linear range was found between 0.25 and 0.75 mM histamine. On the other hand, CPG-ctrl unstably emitted light and exhibited around 100 times higher background intensities than those of CPG even in the absence of histamine. Stimulation with 1 mM histamine seldom lifted the luminescence intensities.

These results of comparison between CPC and CPC-ctrl conclude that circular permutation of GLuc favors the decrease of background intensities. The decreased background luminescence enabled us to determine dynamics of free $Ca^{2+}$ levels triggered by histamine.

Example 13

Saturation Rate of Substrate in COS-7 Cells Carrying pCPG-Ctrl

Figure 22:
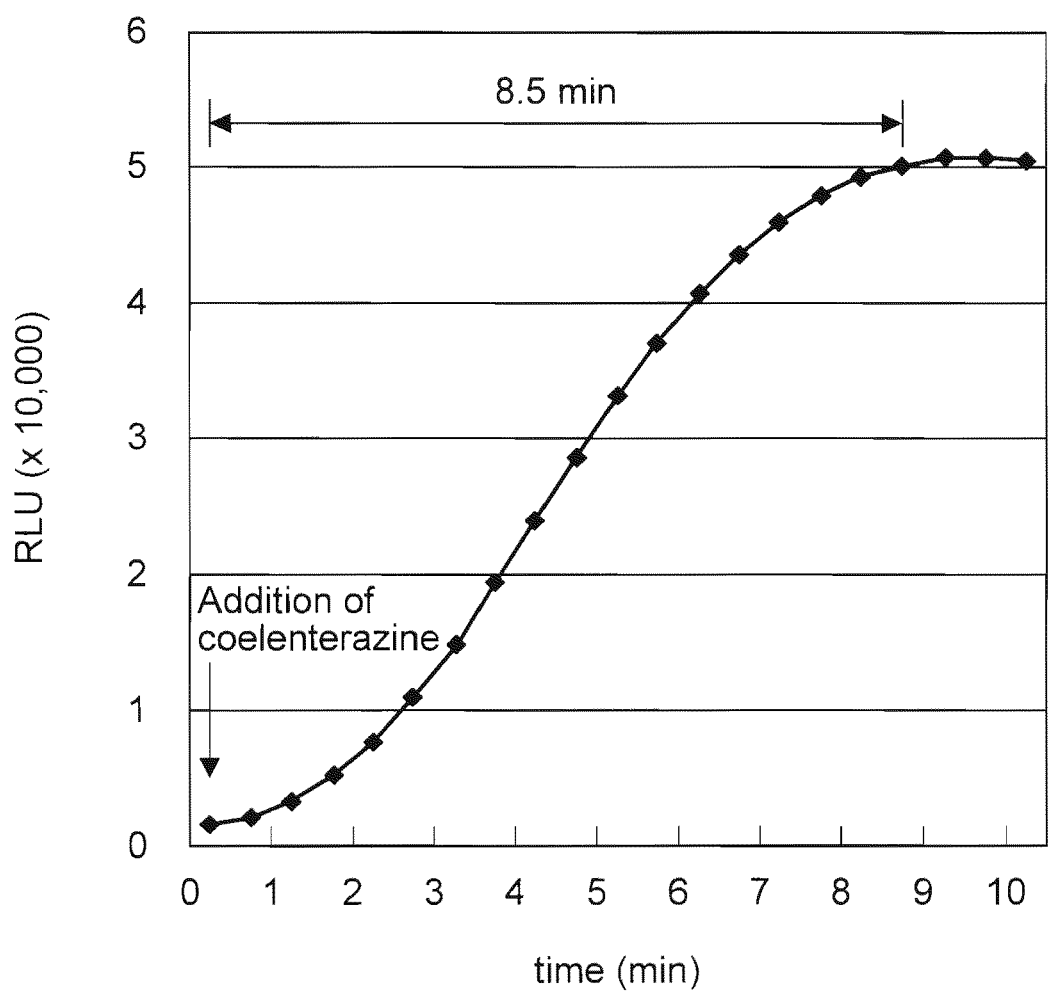
FIG. 22 is a graph showing a saturation rate of coelenterazine in COS-7 cells carrying CPG.

A reaction rate of coelenterazine saturation in COS-7 cells was monitored. As in Example 2, COS-7 cells cultured on a 24-well plate were transiently transfected with pCPG-ctrl and were incubated for 16 hours. The cells on the plate were washed once with HBSS buffer and were saturated with 500 µL HBSS buffer. The luminescence variances after coelenterazine addition were monitored with a biolumines-cence plate reader (Mithras LB 940; Berthold). The results are shown in FIG. 22. As shown in FIG. 22, coelenterazine was absorbed so that the COS-7 cells was saturated in 8.5 minutes.

According to the present invention, it is possible to provide a fusion protein used as a novel single-molecule-format probe. The fusion protein according to the present invention can suppress background enzyme activity and can greatly improve the signal-to-background ratio. This makes it possible to visualize and detect various protein-protein interactions with higher efficiency.

The fusion protein according to the present invention is a single-molecule-format probe, so that a target protein specific ligand can be detected with higher efficiency. This makes it possible to experiment various protein-protein interactions. Thus, the fusion protein according to the present invention is widely applicable to fields such as a bio industry, a drug industry, a food industry, and the like. Particularly, the fusion protein according to the present invention is favorably applicable to a diagnostic medical field, a nanobio field, a pharmacologic action evaluation field, an environment analysis field, and the like.

It is preferable to arrange the fusion protein according to the present invention so that the enzyme is dissected so that at least parts of an active site of the enzyme are respectively located at an amino terminal of the C-terminal fragment and at a carboxy terminal of the N-terminal fragment.

It is preferable that an order of the respective components of the fusion protein according to the present invention is such that: the C-terminal fragment of the enzyme is located downstream of the recognition protein, and the N-terminal fragment is located downstream of the C-terminal fragment, and the ligand binding protein is located downstream of the N-terminal fragment. Further, the recognition protein and the ligand binding protein may be replaced with each other.

It is preferable to arrange the fusion protein according to the present invention so that the ligand binding protein is selected from the group consisting of a nuclear receptor, a cytokine receptor, a protein kinase, a second messenger recognition protein, and a transcription factor.

In the fusion protein according to the present invention, it is preferable that the enzyme is a luciferase, and it is more preferable that a substrate of the luciferase is a firefly luciferin, a *Renilla* luciferin, or a lipid, and it is still more preferable that the luciferase is selected from the group consisting of firefly luciferase, Gaussia luciferase, click beetle luciferase, *Renilla* luciferase, and railroad worm luciferase.

It is preferable to arrange the fusion protein according to the present invention so that the ligand binding protein is a ligand binding domain of an estrogen receptor, and the recognition protein is an SH2 domain of an Src protein, and the luciferase is the click beetle luciferase.

It is preferable to arrange the fusion protein according to the present invention so that the ligand binding protein is an androgen receptor, and the recognition protein is a coactivator, and the luciferase is the firefly luciferase.

It is preferable to arrange the fusion protein according to the present invention so that the ligand binding protein is calmodulin, and the recognition protein is an M13 peptide derived from myosin light chain kinase, and the luciferase is the Gaussia luciferase.

It is preferable that a fusion protein according to the present invention comprises an amino acid sequence specified in any one of SEQ ID Nos: 1 through 3; or a fusion protein, comprising an amino acid sequence, in which one or several amino acids of the amino acid sequence have been deleted, substituted, or added in the amino acid sequence, specified in any one of SEQ ID Nos: 1 through 3, wherein two fragments of a luciferase having been dissected alter luminescence intensity of the luciferase via complementation in case where a recognition protein recognizes that a ligand is bound to a ligand binding protein.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. An isolated chimeric polynucleotide, encoding a fusion protein for detecting an estrogen receptor ligand, the fusion protein comprising:

an estrogen receptor ligand binding protein for binding the estrogen receptor ligand;

a recognition protein for recognizing that the estrogen receptor ligand is bound to the estrogen receptor ligand binding protein; and a C-terminal fragment and an N-terminal fragment of an enzyme located between the estrogen receptor ligand binding protein and the recognition protein, the enzyme having been dissected into the C-terminal fragment and the N-terminal fragment, a carboxy terminal end of the C-terminal fragment being located upstream of an amino terminal end of the N-terminal fragment, and the C-terminal fragment and the N-terminal fragment altering enzyme activity of the enzyme via complementation in case where the recognition protein recognizes that the estrogen receptor ligand is bound to the estrogen receptor ligand binding protein;

wherein the isolated chimeric polynucleotide comprises any one of the following (i) through (iii):

(i) the nucleotide sequence as set forth in SEQ ID No:4;

(ii) the nucleotide sequence which is hybridized with a polynucleotide, having a nucleotide sequence complementary with the nucleotide sequence as set forth in SEQ ID No: 4, under a stringent condition that is a condition under which incubation is performed overnight at 42° C. in a hybridization solution (containing 50% formamide, 5×SSC (150 mM of NaCl, 15 mM of trisodium citrate), 50 mM of sodium phosphate (pH7.6), 5×Denhardt's solution, 10% dextran sulfate, and 20 μg/ml of denatured sheared salmon sperm DNA), and then the resultant is filtered in 0.1×SSC at around 65° C. to be washed; and (iii) a nucleotide sequence which is at least 90% identical to the nucleotide sequence as set forth in SEQ ID No: 4, and wherein said nucleotide sequence of (i), (ii) or (iii) each encodes the fusion protein in which the two fragments of the luciferase having been dissected alter luminescence intensity of the luciferase via complementation in case where the recognition protein recognizes that the estrogen receptor ligand is bound to the estrogen receptor ligand binding protein.

2. A vector, comprising the isolated chimeric polynucleotide as set forth in claim 1.

3. A transformed cell, comprising the isolated chimeric polynucleotide as set forth in claim 1.

4. A transformed cell, comprising the vector as set forth in claim 2.

5. A probe construction kit, comprising the isolated chimeric polynucleotide as set forth in claim 1.

6. A probe construction kit, comprising the vector as set forth in claim 2.

7. An isolated chimeric polynucleotide comprising a nucleotide sequence encoding a fusion protein that is identical to a fusion protein encoded by the nucleotide sequence as set forth in SEQ ID No: 4.

* * * * *